United States Patent
Saint-Remy et al.

(10) Patent No.: US 11,226,332 B2
(45) Date of Patent: Jan. 18, 2022

(54) METHOD FOR THE DETECTION, PREPARATION AND DEPLETION OF CD4+ T LYMPHOCYTES

(71) Applicant: IMCYSE SA, Liège (BE)

(72) Inventors: Jean-Marie Saint-Remy, Grez-Doiceau (BE); Vincent Carlier, Enines (BE); Luc Vander Elst, Obaix (BE)

(73) Assignee: IMCYSE SA, Liege (BE)

( * ) Notice: Subject to any disclaimer, the term of this patent is extended or adjusted under 35 U.S.C. 154(b) by 144 days.

(21) Appl. No.: 16/507,133

(22) Filed: Jul. 10, 2019

(65) Prior Publication Data

US 2020/0103407 A1 Apr. 2, 2020

Related U.S. Application Data

(63) Continuation of application No. 14/894,221, filed as application No. PCT/EP2014/060994 on May 27, 2014, now abandoned.

(30) Foreign Application Priority Data

May 28, 2013 (GB) .................................... 1309469

(51) Int. Cl.

| G01N 33/569 | (2006.01) |
| C07K 14/73 | (2006.01) |
| C07K 14/725 | (2006.01) |
| C07K 17/14 | (2006.01) |
| G01N 33/50 | (2006.01) |
| C07K 14/74 | (2006.01) |
| A61K 39/00 | (2006.01) |

(52) U.S. Cl.
CPC ... *G01N 33/56972* (2013.01); *C07K 14/7051* (2013.01); *C07K 14/70514* (2013.01); *C07K 14/70539* (2013.01); *C07K 17/14* (2013.01); *G01N 33/505* (2013.01); *G01N 33/56977* (2013.01); *A61K 2039/605* (2013.01); *C07K 2319/00* (2013.01); *G01N 2333/70514* (2013.01); *G01N 2333/70539* (2013.01); *G01N 2469/10* (2013.01)

(58) Field of Classification Search
CPC .......... G01N 33/56972; G01N 33/505; G01N 33/56977; C07K 14/0514; C07K 17/14; A61K 2039/605

See application file for complete search history.

(56) References Cited

U.S. PATENT DOCUMENTS

| 4,599,231 A | 7/1986 | Milich et al. |
| 4,886,782 A | 12/1989 | Good et al. |
| 5,433,948 A | 7/1995 | Thomas et al. |
| 5,552,142 A | 9/1996 | Thomas et al. |
| 5,589,175 A | 12/1996 | Vahlne et al. |
| 5,633,234 A | 5/1997 | August et al. |
| 5,736,142 A | 4/1998 | Sette et al. |
| 5,770,202 A | 6/1998 | Thomas et al. |
| 5,773,002 A | 6/1998 | Thomas et al. |
| 5,863,528 A | 1/1999 | Hawley et al. |
| 6,399,383 B1 | 6/2002 | Apt et al. |
| 6,602,509 B1 | 8/2003 | Saint-Remy et al. |
| 6,656,471 B1 | 12/2003 | Sastry et al. |
| 6,759,046 B1 | 7/2004 | Gaudernack et al. |
| 7,157,089 B1 | 1/2007 | Mizzen et al. |
| 7,306,804 B2 | 12/2007 | Sastry et al. |
| 7,780,882 B2 | 8/2010 | Chang et al. |
| 8,999,346 B2 | 4/2015 | Saint-Remy |
| 9,044,507 B2 | 6/2015 | Saint-Remy |
| 9,248,171 B2 | 2/2016 | Saint-Remy |
| 9,249,202 B2 | 2/2016 | Saint-Remy |

(Continued)

FOREIGN PATENT DOCUMENTS

| JP | 2004147649 A | 5/2004 |
| WO | WO-8504103 A1 | 9/1985 |

(Continued)

OTHER PUBLICATIONS

Carlier et al. Increased Synapse Formation Obtained by T Cell Epitopes Containing a CxxC Motif in Flanking Residues Convert CD4+ T Cells Into Cytolytic Effectors. PLOS ONE 7(10): e45366 pp. 1-18 (Oct. 2012).*

U.S. Appl. No. 12/377,048, filed Feb. 10, 2009, U.S. Pat. No. 9,249,202, Feb. 2, 2019.

U.S. Appl. No. 14/976,259, filed Dec. 21, 2015, US 2016-0194367 A1, Jul. 7, 2016.

U.S. Appl. No. 12/735,744, filed Aug. 13, 2010, U.S. Pat. No. 9,248,171, Feb. 2, 2016.

U.S. Appl. No. 14/980,932, filed Dec. 28, 2015, US 2016-0108103 A1, Apr. 21, 2016.

(Continued)

*Primary Examiner* — Gailene Gabel
(74) *Attorney, Agent, or Firm* — Nixon & Vanderhye, PC

(57) ABSTRACT

The present invention relates an in vitro method for detecting class II restricted CD4+ T cells in a sample. Herein a sample is contacted with an isolated complex of an MHC class II molecule and a peptide. This peptide comprises an MHC class II restricted T cell epitope of an antigenic protein and immediately adjacent thereof, or separated by a linker of at most 7 amino acids a sequence with a [CST]-xx-C or C-xx-[CST] motif. CD4+ T cells are detected by measuring the binding of the complex with cells in the sample, wherein the binding of the complex to a cell is indicative for the presence of CD4+ T cells in the sample. The present invention further relates to an isolated complex of an MHC Class II molecule and a peptide comprising an MHC class II restricted T cell epitope of an antigenic protein and immediately adjacent thereof, or separated by a linker of at most 7 amino acids a sequence with a [CST]-xx-C or C-xx-[CST] motif.

21 Claims, No Drawings

Specification includes a Sequence Listing.

(56) References Cited

U.S. PATENT DOCUMENTS

| | | | |
|---|---|---|---|
| 9,394,517 B2 | 7/2016 | Saint-Remy | |
| 9,861,661 B2 | 1/2018 | Saint-Remy | |
| 10,023,847 B2 | 7/2018 | Saint-Remy | |
| 2003/0049723 A1 | 3/2003 | Zhang et al. | |
| 2003/0104570 A1 | 6/2003 | Cabezon et al. | |
| 2003/0129205 A1 | 7/2003 | Saint-Remy et al. | |
| 2003/0152581 A1 | 8/2003 | Saint-Remy et al. | |
| 2004/0077045 A1 | 4/2004 | Zhang et al. | |
| 2005/0107256 A1 | 5/2005 | Barnwell et al. | |
| 2005/0196386 A1 | 9/2005 | Blazar et al. | |
| 2005/0202044 A1 | 9/2005 | Mizzen et al. | |
| 2006/0182763 A1 | 8/2006 | Kim et al. | |
| 2006/0211091 A1 | 9/2006 | Zhang et al. | |
| 2006/0216301 A1 | 9/2006 | Tahara et al. | |
| 2006/0269561 A1 | 11/2006 | Paterson et al. | |
| 2007/0160620 A1 | 7/2007 | Mizzen et al. | |
| 2007/0184023 A1 | 8/2007 | Rasmussen et al. | |
| 2008/0176247 A1 | 7/2008 | Chou et al. | |
| 2009/0012004 A1 | 1/2009 | Sette et al. | |
| 2010/0033088 A1 | 2/2010 | Hwang et al. | |
| 2010/0068193 A1 | 3/2010 | Brunsvig et al. | |
| 2010/0183652 A1 | 7/2010 | Page et al. | |
| 2010/0203083 A1 | 8/2010 | Lux et al. | |
| 2010/0303866 A1* | 12/2010 | Saint-Remy | A61P 37/02 424/275.1 |
| 2010/0330088 A1 | 12/2010 | Saint-Remy | |
| 2011/0111395 A1 | 5/2011 | Saint-Remy | |
| 2012/0009678 A1 | 1/2012 | Saint-Remy | |
| 2013/0095133 A1 | 4/2013 | Klatzmann et al. | |
| 2014/0370044 A1 | 12/2014 | Saint-Remy | |
| 2014/0377299 A1 | 12/2014 | Saint-Remy | |
| 2015/0110821 A1 | 4/2015 | Saint-Remy | |
| 2016/0091492 A1 | 3/2016 | Saint-Remy et al. | |
| 2016/0108103 A1 | 4/2016 | Saint-Remy | |
| 2016/0194367 A1 | 7/2016 | Saint-Remy | |
| 2016/0250255 A1 | 9/2016 | Saint-Remy et al. | |
| 2016/0339121 A1 | 11/2016 | Saint-Remy et al. | |
| 2017/0100466 A1 | 4/2017 | Saint-Remy | |
| 2018/0228912 A1 | 8/2018 | Saint-Remy et al. | |
| 2018/0258154 A1 | 9/2018 | Saint-Remy et al. | |
| 2018/0346887 A1 | 12/2018 | Saint-Remy | |
| 2019/0106477 A1 | 4/2019 | Vander | |

FOREIGN PATENT DOCUMENTS

| | | |
|---|---|---|
| WO | WO-9205800 A1 | 4/1992 |
| WO | WO-9308279 A1 | 4/1993 |
| WO | WO-9405790 A1 | 3/1994 |
| WO | WO-9740852 A1 | 11/1997 |
| WO | WO-9958552 A2 | 11/1999 |
| WO | WO-0029008 A2 | 5/2000 |
| WO | WO-0155393 A2 | 8/2001 |
| WO | WO-0170263 A1 | 9/2001 |
| WO | WO-0200892 A1 | 1/2002 |
| WO | WO-02095051 A2 | 11/2002 |
| WO | WO-02097070 A1 | 12/2002 |
| WO | WO-03072731 A2 | 9/2003 |
| WO | WO-2004018667 A1 | 3/2004 |
| WO | WO-2004024766 A1 | 3/2004 |
| WO | WO-2005012502 A2 | 2/2005 |
| WO | WO-2005039613 A1 | 5/2005 |
| WO | WO-2005042575 A2 | 5/2005 |
| WO | WO-2005086781 A2 | 9/2005 |
| WO | WO-2006009920 A2 | 1/2006 |
| WO | WO-2006059529 A1 | 6/2006 |
| WO | WO-2007027954 A2 | 3/2007 |
| WO | WO-2007104715 A2 | 9/2007 |
| WO | WO-2007135684 A2 | 11/2007 |
| WO | WO-2008017517 A1 | 2/2008 |
| WO | WO-2009042215 A2 | 4/2009 |
| WO | WO-2009042215 A3 | 7/2009 |
| WO | WO-2009100505 A1 | 8/2009 |
| WO | WO-2009101201 A2 | 8/2009 |
| WO | WO-2009101204 A2 | 8/2009 |
| WO | WO-2009101205 A2 | 8/2009 |
| WO | WO-2009101206 A2 | 8/2009 |
| WO | WO-2009101207 A1 | 8/2009 |
| WO | WO-2009101208 A2 | 8/2009 |
| WO | WO-2009106073 A2 | 9/2009 |
| WO | WO-2010037395 A2 | 4/2010 |
| WO | WO-2010115046 A2 | 10/2010 |
| WO | WO-2012069568 A2 | 5/2012 |
| WO | WO-2013113076 A1 | 8/2013 |
| WO | WO-2013121296 A1 | 8/2013 |
| WO | WO-2014191432 A1 | 12/2014 |
| WO | WO-2015063176 A1 | 5/2015 |
| WO | WO-2016059236 A1 | 4/2016 |

OTHER PUBLICATIONS

U.S. Appl. No. 12/735,739, filed Aug. 13, 2010, US 2010-0330088 A1, Dec. 30, 2010.

U.S. Appl. No. 15/388,398, filed Dec. 22, 2016, US 2017-0100466 A1, Apr. 13, 2017.

U.S. Appl. No. 12/735,740, filed Aug. 13, 2010, U.S. Pat. No. 8,999,346, Apr. 7, 2015.

U.S. Appl. No. 14/589,134, filed Jan. 5, 2015, US-2015-0110821-A1, Apr. 23, 2015.

U.S. Appl. No. 12/735,742, filed Aug. 13, 2010, US 2012-0009678 A1, Jan. 12, 2012.

U.S. Appl. No. 14/450,722, filed Aug. 4, 2014, US 2014-0377299 A1, Dec. 25, 2014.

U.S. Appl. No. 13/988,925, filed Jun. 6, 2013, U.S. Pat. No. 10,023,847, Jul. 17, 2018.

U.S. Appl. No. 16/008,399, filed Jun. 14, 2018, US 2018-0346887 A1, Dec. 6, 2018.

U.S. Appl. No. 14/375,324, filed Jul. 29, 2014, US 2014-0370044 A1, Dec. 18, 2014.

U.S. Appl. No. 14/894,221, filed Nov. 25, 2015, US 2016-0091492 A1, Mar. 31, 2016.

U.S. Appl. No. 15/516,045, filed Mar. 31, 2017, US 2018-0228912 A1, Aug. 16, 2018.

U.S. Appl. No. 16/091,549, filed Oct. 5, 2018, US 2019-0106477 A1, Apr. 11, 2019.

U.S. Appl. No. 15/151,868, filed May 11, 2016, US 2016-0339121 A1, Nov. 24, 2016.

U.S. Appl. No. 15/761,223, filed Mar. 19, 2018, US 2018-0258154 A1, Sep. 13, 2018.

U.S. Appl. No. 12/735,754, filed Aug. 13, 2010, U.S. Pat. No. 9,044,507, Jun. 2, 2015.

U.S. Appl. No. 14/686,855, filed Apr. 15, 2015, U.S. Pat. No. 9,861,661, Jan. 9, 2018.

Abrahimians, E.M., et al., "MHC Class II-Restricted Epitopes Containing an Oxidoreductase Activity Prompt CD4+ T Cells with Apoptosis-Inducing Properties," Frontiers in Immunology, 6:1-5, Frontiers Research Foundation, Switzerland (Sep. 2015).

Abrahimians, E.M., et al., "Thioreductase-Containing Epitopes Inhibit the Development of Type 1 Diabetes in the NOD Mouse Model," Frontiers in Immunology, 7:1-10, Frontiers Research Foundation, Switzerland (Mar. 2016).

Advisory Action dated Feb. 4, 2019, in U.S. Appl. No. 14/976,259, Saint-Remy, J.M., filed Dec. 21, 2015, 3 pages.

Advisory Action dated Jun. 27, 2014, in U.S. Appl. No. 12/735,739, Saint-Remy, J.M., filed Aug. 13, 2010, 3 pages.

Advisory Action dated Mar. 20, 2017, in U.S. Appl. No. 14/589,134, Saint-Remy, J.M., filed Jan. 5, 2015, 3 pages.

Advisory Action dated May 9, 2018, in U.S. Appl. No. 14/450,722, Saint-Remy, J.M., filed Aug. 4, 2014, 3 pages.

Advisory Action dated Oct. 22, 2013, in U.S. Appl. No. 12/735,740, Saint-Remy, J.M., filed Aug. 13, 2010, 3 pages.

Aleksza, M., et al., "Altered Cytokine Expression of Peripheral Blood Lymphocytes in Polymyositis and Dermatomyositis," Annals of the Rheumatic Diseases, 64(10):1485-1489, BMJ, England (Oct. 2005).

Aley, S.B. and Gillin, F.D., "Giardia Lamblia: Post-Translational Processing and Status of Exposed Cysteine Residues in TSA 417, A

(56) References Cited

OTHER PUBLICATIONS

Variable Surface Antigen," Experimental Parasitology, 77(3):295-305, Academic Press, United States (Nov. 1993).
Ali-Khan, N., et al., "Overview of Proteome Analysis," Current Protocols in Protein Science, 30(1):22.1.1-22.1.19, Hoboken, NJ : Wiley Interscience, United States (Dec. 2002).
Apostolou, I., et al., "Evidence for Two Subgroups of CD4-CD8-NKT Cells With Distinct TCR Alpha Beta Repertoires and Differential Distribution in Lymphoid Tissues," Journal of Immunology, 165(5):2481-2490, American Association of Immunologists, United States (Sep. 2000).
Appella, E., et al., "Analysis of the Structure of Naturally Processed Peptides Bound by Class I and Class II Major Histocompatibility Complex Molecules," EXS, 73:105-119, Birkhäuser Verlag, Switzerland (1995).
Arunachalam, B., et al., "Enzymatic Reduction of Disulfide Bonds in Lysosomes: Characterization of a Gamma-interferon-inducible Lysosomal Thiol Reductase (GILT)," Proceedings of the National Academy of Sciences of the United States of America, 97(2):745-750, National Academy of Sciences, United States (Jan. 2000).
Ascherio, A., "Environmental Factors in Multiple Sclerosis," Expert Review of Neurotherapeutics, 13(12 Suppl):3-9, Taylor & Francis, England (Dec. 2013).
Azoury-Ziadeh, R., et al., "T-Helper Epitopes Identified Within the E6 Transforming Protein of Cervical Cancer-Associated Human Papillomavirus Type 16," Viral Immunology, 12(4):297-312, Mary Ann Liebert, Inc., United States (1999).
Balato, A., et al., "Natural Killer T Cells: an Unconventional T-Cell Subset With Diverse Effector and Regulatory Functions," The Journal of Investigative Dermatology, 129(7):1628-1642, Elsevier, United States (Jul. 2009).
Batten, P., et al., "Immune Response to Stem Cells and Strategies to Induce Tolerance," Philosophical Transactions of the Royal Society of London. Series B, Biological Sciences, 362(1484):1343-1356, Royal Society, England (Aug. 2007).
Boisgerault, F., et al., "Differential Roles of Direct and Indirect Allorecognition Pathways in the Rejection of Skin and Corneal Transplants," Transplantation, 87(1):16-23, Lippincott Williams & Wilkins, United States (Jan. 2009).
Bolivar, J., et al., "Molecular Cloning of a Zinc Finger Autoantigen Transiently Associated With Interphase Nucleolus and Mitotic Centromeres and Midbodies. Orthologous Proteins With Nine CXXC Motifs Highly Conserved From Nematodes to Humans," The Journal of Biological Chemistry, 274(51):36456-36464, American Society for Biochemistry and Molecular Biology, United States (Dec. 1999).
Bower, M.S., et al., "Two Members of the Thioredoxin-h Family Interact With the Kinase Domain of a *Brassica* S *locus* Receptor Kinase," The Plant Cell, 8(9):1641-1650, American Society for Biochemistry and Molecular Biology, United States (Sep. 1996).
Braun, M.Y et al., "Acute Rejection in the Absence of Cognate Recognition of Allograft by T Cells," Journal of Immunology, 166(8):4879-4883, American Association of Immunologists, United States (Apr. 2001).
Brinks, V., et al., "Immunogenicity of Therapeutic Proteins: The Use of Animal Models," Pharmaceutical Research, 28(10):2379-2385, Kluwer Academic/Plenum Publishers, United States (Oct. 2011).
Brinster, C. and Shevach, E.M., "Bone Marrow-Derived Dendritic Cells Reverse the Anergic State of CD4+CD25+ T Cells without Reversing Their Suppressive Function," Journal of Immunology, 175(11):7332-7340, American Association of Immunologists, United States (Dec. 2005).
Brinster, C. and Shevach, E.M., "Costimulatory Effects of IL-1 on the Expansion/differentiation of CD4+CD25+Foxp3+ and CD4+CD25+Foxp3-T Cells," Journal of Leukocyte Biology, 84(2):480-487, Wiley on behalf of the Society for Leukocyte Biology, United States (Aug. 2008).

Cao, O., et al., "Prevention of Gene Transfer-Induced Inhibitor Formation by Nasal Administration of Human F.IX T Cell Epitope in a Murine Model of Hemophilia B," Blood, 104(11):414, Nov. 2004).
Capon, D.J. and Ward, R.H., "The CD4-gp120 Interaction and Aids Pathogenesis," Annual Review of Immunology, 9:649-678, Annual Reviews Inc., United States (1991).
Carlier, V.A., et al., "Control of Asthma by in Vitro-Induced Allergen-Specific Regulatory T Cells in the Mouse," Munksgaard Allergy, 65:555, Jun. 2007).
Carlier, V.A., et al., "Increased Synapse Formation Obtained by T cell Epitopes Containing a CxxC Motif in Flanking Residues Convert CD4+ T Cells into Cytolytic Effectors," PLOS One, 7(10):e45366, Public Library of Science, United States (Oct. 2012).
Caro-Aguilar, I., et al., "Chimeric Epitopes Delivered by Polymeric Synthetic Linear Peptides Induce Protective Immunity to Malaria," Microbes and Infection, 7(13):1324-1337, Elsevier, France (Oct. 2005).
Castano, A.R., et al., "Peptide Binding and Presentation by Mouse CD1," Science, 269(5221):223-226, American Association for the Advancement of Science, United States (Jul. 1995).
Cavone, L., et al., "Long-Term Suppression of EAE Relapses by Pharmacological Impairment of Epitope Spreading," British Journal of Pharmacology, 171(6):1501-1509, Wiley, England (Mar. 2014).
Celis, E., et al., "Identification of Potential CTL Epitopes of Tumor-associated Antigen MAGE-1 for Five Common HLA-A Alleles," Molecular Immunology, 31(18):1423-1430, Pergamon Press, England (Dec. 1994).
Celis, E., et al., "Induction of Anti-Tumor Cytotoxic T Lymphocytes in Normal Humans Using Primary Cultures and Synthetic Peptide Epitopes," Proceedings of the National Academy of Sciences of the United States of America, 91(6):2105-2109, National Academy of Sciences, United States (Mar. 1994).
Chen, T.C., et al., "Induction of Dominant Transplantation Tolerance by an Altered Peptide Ligand of the Male Antigen Dby," The Journal of Clinical Investigation, 113(12):1754-1762, American Society for Clinical Investigation, United States (Jun. 2004).
Chen, X., et al., "Glucocorticoid Amplifies IL-2-Dependent Expansion of Functional FoxP3(+)CD4(+)CD25(+) T Regulatory Cells in Vivo and Enhances Their Capacity to Suppress EAE," European Journal of Immunology, 36(8):2139-2149, Wiley-VCH, Germany (Aug. 2006).
Chaunlin ed., Molecular Immunology, pp. 428-429, 433-436, 15 pages, Fudan University Press, Shanghai Medical College Press, (May 2001) (English Language Translation Provided).
Corthay, A., "CD4+ T Cells Cooperate With Macrophages for Specific Elimination of MHC Class II-Negative Cancer Cells," Advances in Experimental Medicine and Biology, 590:195-208, Kluwer Academic/Plenum Publishers, United States (2007).
Cotton, N.J., et al., "Oxidative Inhibition of Human Soluble Catechol-O-Methyltransferase," The Journal of Biological Chemistry, 279(22):23710-23718, American Society for Biochemistry and Molecular Biology, United States (May 2004).
Credo Reference, 2012.
Crellin, N.K., et al., "Altered Activation of AKT is Required for the Suppressive Function of Human CD4+CD25+ T Regulatory Cells," Blood, 109(5):2014-2022, American Society of Hematology, United States (Mar. 2007).
Crompton, P.D., et al., "Advances and Challenges in Malaria Vaccine Development," The Journal of Clinic Investigation, 120(12):4168-4178, American Society for Clinical Investigation, United States (Dec. 2010).
Davids, B.J., et al., "A New Family of Giardial Cysteine-rich Non-VSP Protein Genes and a Novel Cyst Protein," PLoS One, 1:e44, Public Library of Science, United States (Dec. 2006).
Davids, M.M., et al., "Interrogating the Repertoire: Broadening the Scope of Peptide-MHC Multimer Analysis," Nature Reviews. Immunology, 11(8):551-558, Nature Pub. Group, England (Jul. 2011).
De Groot, A.S. and Scott, D.W., "Immunogenicity of Protein Therapeutics," Trends in Immunology, 28(11):482-490, Elsevier Science Ltd., England (Nov. 2007).
De La Cruz, V.F., et al., "The Immunologic Significance of Variation Within Malaria Circumsporozoite Protein Sequences," Journal of

(56) References Cited

OTHER PUBLICATIONS

Immunology, 142(10):3568-3575, American Association of Immunologists, United States (May 1989).
Desmetz, C., et al., "Proteomics-Based Identification of HSP60 as a Tumor-Associated Antigen in Early Stage Breast Cancer and Ductal Carcinoma in situ," Journal of Proteome Research, 7(9):3830-3837, American Chemical Society, United States (Sep. 2008).
Dobrzanski, M.J., "Expanding Roles for CD4 T Cells and Their Subpopulations in Tumor Immunity and Therapy," Frontiers in Oncology, 3:1-19, Frontiers Research Foundation, Switzerland (Mar. 2013).
Dobrzynski, E., et al., "Prevention of Cytotoxic T Lymphocyte Responses to Factor IX-Expressing Hepatocytes by Gene Transfer-induced Regulatory T Cells," Proceedings of the National Academy of Sciences of the United States of America, 103(12):4592-4597, National Academy of Sciences, United States (Mar. 2006).
Eberl, G., et al., "Tissue-specific Segregation of CD1d-dependent and CD1d-independent NK T Cells," Journal of Immunology, 162(11):6410-6419, American Association of Immunologists, United States (Jun. 1999).
Facktor, M.A., et al., "Hypersensitivity to Tetanus Toxoid," The Journal of Allergy and Clinical Immunology, 52(1):1-12, Mosby, United States (Jul. 1973).
Fan, C.F. and Mei, X.G., "Co-Immunization of BALB/c Mice With Recombinant Immunogens Containing G Protein Fragment and Chimeric CTL Epitope of Respiratory Syncytial Virus Induces Enhanced Cellular Immunity and High Level of Antibody Response," Vaccine, 23(35):4453-4461, Elsevier Science, Netherlands (Aug. 2005).
Final Office Action dated Apr. 15, 2019, in U.S. Appl. No. 15/388,398, Saint-Remy, J.M., filed Dec. 22, 2016, 15 pages.
Final Office Action dated Aug. 31, 2016 in U.S. Appl. No. 12/735,739, Saint-Remy, J.M., filed Aug. 13, 2010, 12 Pages.
Final Office Action dated Aug. 7, 2019, in U.S. Appl. No. 15/516,045, Saint-Remy, J.M., et al., filed Mar. 31, 2017, 5 pages.
Final Office Action dated Aug. 9, 2012, in U.S. Appl. No. 12/377,048, Saint-Remy, J.M., filed Feb. 10, 2009, 9 pages.
Final Office Action dated Dec. 2, 2016, in U.S. Appl. No. 14/589,134, Saint-Remy, J.M., filed Jan. 5, 2015, 14 pages.
Final Office Action dated Dec. 28, 2016, in U.S. Appl. No. 13/988,925, Saint-Remy, J.M., filed Jun. 6, 2013, 5 pages.
Final Office Action dated Dec. 28, 2017, in U.S. Appl. No. 14/450,722, Saint-Remy, J.M., filed Aug. 4, 2014, 10 pages.
Final Office Action dated Feb. 13, 2019, in U.S. Appl. No. 15/516,045, Saint-Remy, J.M., et al., filed Mar. 31, 2017, 5 pages.
Final Office Action dated Feb. 20, 2014 in U.S. Appl. No. 12/735,739, Saint-Remy, J.M., filed Aug. 13, 2010, 10 Pages.
Final Office Action dated Jan. 19, 2018, in U.S. Appl. No. 14/589,134, Saint-Remy, J.M., filed Jan. 5, 2015, 15 pages.
Final Office Action dated Jan. 20, 2012, in U.S. Appl. No. 12/377,048, Saint-Remy, J.M., filed Feb. 10, 2009, 10 pages.
Final Office Action dated Jan. 8, 2019, in U.S. Appl. No. 14/980,932, Saint-Remy, J.M., filed Dec. 28, 2015.
Final Office Action dated Jul. 10, 2013, in U.S. Appl. No. 12/735,740, Saint-Remy, J.M., filed Aug. 13, 2010, 14 pages.
Final Office Action dated Jun. 5, 2015, in U.S. Appl. No. 12/735,744, Saint-Remy, J.M., filed Aug. 13, 2010, 11 pages.
Final Office Action dated Jun. 6, 2019, in U.S. Appl. No. 14/450,722, Saint-Remy, J.M., filed Aug. 4, 2014, 8 pages.
Final Office Action dated Mar. 19, 2019, in U.S. Appl. No. 15/151,868, Saint-Remy, J.M., et al., filed May 11, 2016, 19 pages.
Final Office Action dated Mar. 25, 2019, in U.S. Appl. No. 14/375,324, Saint-Remy, J.M., filed Jul. 29, 2014, 14 pages.
Final Office Action dated May 20, 2014, in U.S. Appl. No. 12/735,744, Saint-Remy, J.M., filed Aug. 13, 2010, 10 Pages.
Final Office Action dated Oct. 26, 2018, in U.S. Appl. No. 14/976,259, Saint-Remy, J.M., filed Dec. 21, 2015, 15 pages.
Final Office Action dated Oct. 30, 2017, in U.S. Appl. No. 14/375,324, Saint-Remy, J.M., filed Jul. 29, 2014, 5 Pages.

Fomenko, D.E. and Gladyshev, V.N., "Identity and Functions of Cxxc-derived Motifs," Biochemistry, 42(38):11214-11225, American Chemical Society, United States (Sep. 30, 2003).
Fournier, P. and Schirrrnacher, V., "Randomized Clinical Studies of Anti-tumor Vaccination: State of the Art in 2008," Expert Review of Vaccines, 8(1):51-66, Taylor & Francis, England (Jan. 2009).
Francois, V., et al., "The CD4(+) T-cell Response of Melanoma Patients to a MAGE-A3 Peptide Vaccine Involves Potential Regulatory T Cells," Cancer Research, 69(10):4335-4345, American Association for Cancer Research, United States (May 15, 2009).
Frankel, A.E., et al., "Characterization of Diphtheria Fusion Proteins Targeted to the Human lnterleukin-3 Receptor," Protein Engineering, 13(8):575-581, Oxford University Press, England (Aug. 2000).
Ge, F.F., et al., "An Hsp70 Fusion Protein Vaccine Potentiates the Immune Response Against Japanese Encephalitis Virus," Archives of Virology, 152(1):125-135, Springer-Verlag, Austria (Jan. 2007).
Geluk, A., et al., "HLA-DR Binding Analysis of Peptides From Islet Antigens in IDDM," Diabetes, 47(10):1594-1601, American Diabetes Association, United States (Oct. 1998).
GenBank FPAA051928, 1997, p. 1.
Geneseq Database, Accession No. BDK51134, "Human Preproinsulin (PPI) Antigenic Peptide, SEQ ID 164," XP002770300, Jan. 26, 2017, Retrieved from EBI accession No. GSP:BDK51134.
GenPept Pdb 5GSB_A, 2017, pp. 1-2.
Gentile, F., et al., "Thyroglobulin as an Autoantigen: What Can We Learn About Immunopathogenicity From the Correlation of Antigenic Properties With Protein Structure?," Immunology, 112(1):13-25, Blackwell Scientific Publications, England (May 2004).
Girardi, E., et al., "Structure of an A-helical Peptide and Lipopeptide Bound to the Nonclassical Major Histocompatibility Complex (MHC) Class I Molecule CD1d," The Journal of Biological Chemistry, 291 (20):10677-10683, American Society for Biochemistry and Molecular Biology, United States (May 13, 2016).
Gross, D.A., et al., "Simple Conditioning With Monospecific CD4+ CD25+ Regulatory T Cells for Bone Marrow Engraftment and Tolerance to Multiple Gene Products," Blood, 108(6):1841-1848, American Society of Hematology, United States (Sep. 15, 2006).
Grossman, W.J., et al., "Differential Expression of Granzymes a and B in Human Cytotoxic Lymphocyte Subsets and T Regulatory Cells," Blood, 104(9):2840-2848, American Society of Hematology, United States (Nov. 2004).
Haga, J.A., et al., "HLA-A, Partial [*Homo sapiens*]," GenBank: AAA59610.1, 1995, p. 1.
Haque, M.A., et al., "Cysteinylation of Mhc Class Ii Ligands: Peptide Endocytosis and Reduction Within Apc Influences T Cell Recognition," Journal of Immunology (Baltimore, Md. : 1950), 166(7):4543-4551, American Association of Immunologists, United States (Apr. 1, 2001).
Harris, S.J., et al., "Prediction of Murine Mhc Class I Epitopes in a Major House Dust Mite Allergen and Induction of T1-type CD8+ T Cell Responses," International Immunology, 9(2):273-280, Oxford University Press, England (Feb. 1997).
Haveman, L.M et al., "Induction and Capture of CD4+ Cytotoxic Adenoviral Specific T-Cells in Response to pan-DR Binding Adenoviral Epitopes; towards Immunotherapy," Blood, 106(11):3238, American Society of Hematology, United States (Nov. 2005).
Haveman, L.M., et al., "Novel Pan-DR-binding T Cell Epitopes of Adenovirus Induce Pro-inflammatory Cytokines and Chemokines in Healthy Donors," International Immunology, 18(11):1521-1529, Oxford University Press, 1989, England (Nov. 2006).
Heemskerk, B., et al., "Adenovirus-specific CD4+ T Cell Clones Recognizing Endogenous Antigen Inhibit Viral Replication in Vitro Through Cognate Interaction," Journal of Immunology (Baltimore, Md. : 1950), 177(12):8851-8859, American Association of Immunologists, United States (Dec. 15, 2006).
Hemmer, B., et al., "Minimal Peptide Length Requirements for CD4(+) T Cell Clones—implications for Molecular Mimicry and T Cell Survival," International Immunology, 12(3):375-383, Oxford University Press, 1989, England (Mar. 2000).
Heurtault, B., et al., "Design of a Liposomal Candidate Vaccine Against Pseudomonas Aeruginosa and Its Evaluation in Triggering

(56) References Cited

OTHER PUBLICATIONS

Systemic and Lung Mucosal Immunity," Pharmaceutical Research, 26(2):276-285, Kluwer Academic/Plenum Publishers, United States (Feb. 2009).
HLA Nomenclature, 2015.
Ho, L.P., et al., "CD4(-)CD8alphaalpha Subset of CD1d-restricted NKT Cells Controls T Cell Expansion," Journal of Immunology (Baltimore, Md. : 1950), 172(12):7350-7358, American Association of Immunologists, United States (Jun. 2004).
Hohn, H., et al., "CD4+ Tumor-infiltrating Lymphocytes in Cervical Cancer Recognize HLA-DR-restricted Peptides Provided by Human Papillomavirus-E7," Journal of Immunology (Baltimore, Md. : 1950), 163(10):5715-5722, American Association of Immunologists, United States (Nov. 15, 1999).
Hori, S., et al., "Control of Regulatory T Cell Development by the Transcription Factor Foxp3," Science, 299(5609):1057-1061, American Association for the Advancement of Science, United States (Feb. 2003).
Hsu, H.J., et al., "Assessing Computational Amino Acid Beta-turn Propensities With a Phage-displayed Combinatorial Library and Directed Evolution," Structure (London, England : 1993), 14(10):1499-1510, Cambridge, Mass. : Cell Press, United States (Oct. 2006).
International Search Report and Written Opinion for International Application No. PCT/EP2015/074063, European Patent Office, Netherlands, dated Jan. 29, 2016, 8 Pages.
International Search Report and Written Opinion for International Application No. PCT/EP2017/059302, European Patent Office, Netherlands, dated Jun. 26, 2017, 11 Pages.
International Search Report and Written Opinion for International Application No. PCT/EP2018/055501, European Patent Office, Netherlands, dated May 4, 2018, 13 Pages.
International Search Report for International Application No. PCT/BE2008/000010, European Patent Office, Germany, dated Jul. 2, 2008.
International Search Report for International Application No. PCT/BE2013/000006, European Patent Office, Netherlands, dated Jul. 1, 2013, 8 Pages.
International Search Report for International Application No. PCT/EP2007/007165, European Patent Office, Netherlands, dated Jan. 17, 2008.
International Search Report for International Application No. PCT/EP2009/051803, European Patent Office, Netherlands, dated Aug. 11, 2009, 5 Pages.
International Search Report for International Application No. PCT/EP2009/051804, European Patent Office, Netherlands, dated Aug. 11, 2009, 6 Pages.
International Search Report for International Application No. PCT/EP2009/051806, European Patent Office, Netherlands, dated Aug. 11, 2009, 6 Pages.
International Search Report for International Application No. PCT/EP2009/051807, European Patent Office, Netherlands, dated Jul. 13, 2009, 5 Pages.
International Search Report for International Application No. PCT/EP2009/051808, European Patent Office, Netherlands, dated Feb. 18, 2010, 7 Pages.
International Search Report for International Application No. PCT/EP2014/060994, European Patent Office, Netherlands, dated Sep. 18, 2014, 5 pages.
Iqbalsyah, T.M., et al., "The CXXC Motif at the N Terminus of an Alpha-helical Peptide," Protein Science : a Publication of the Protein Society, 15(8):1945-1950, Cold Spring Harbor Laboratory Press, United States (Aug. 2006).
Ise, W., et al., "Naive CD4+ T Cells Exhibit Distinct Expression Patterns of Cytokines and Cell Surface Molecules on Their Primary Responses to Varying Doses of Antigen," Journal of Immunology (Baltimore, Md. : 1950), 168(7):3242-3250, American Association of Immunologists (Apr. 2002).
James, E., et al., "HY Peptides Modulate Transplantation Responses to Skin Allografts," International Immunology, 14(11):1333-1342, Oxford University Press, 1989, England (Nov. 2002).
Janeway, C.A., et al., "Immunobiology, 3rd edition," Garland Press Inc., 1997, p. 11.
Janssens, W., et al., "CD4+CD25+ T Cells Lyse Antigen-presenting B Cells by Fas-fas Ligand Interaction in an Epitope-specific Manner," Journal of immunology (Baltimore, Md. : 1950), 171(9):4604-4612, American Association of Immunologists, United States (Nov. 2003).
Jensen, P.E., "Acidification and Disulfide Reduction Can be Sufficient to Allow Intact Proteins to Bind Class II MHC," Journal of Immunology, 150(8 Pt 1):3347-3356, American Association of Immunologists, United States (Apr. 1993).
Jiang, E.P., et al., "Protection by the Gross Saponins of Tribulus Terrestris Against Cerebral Ischemic Injury in Rats Involves the NF-KB Pathway," Acta Pharmaceutica Sinica B, 1(1):21-26, (Jun. 2011).
Joffre, O., et al., "Induction of Antigen-specific Tolerance to Bone Marrow Allografts With CD4+CD25+ T Lymphocytes," Blood, 103(11):4216-4221, American Society of Hematology, United States (Jun. 1, 2004).
Karin, N., et al., "Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production," The Journal of Experimental Medicine, 180(6):2227-2237, Rockefeller University Press, United States (Dec. 1, 1994).
Kasprowicz, V., et al., "Tracking of Peptide-specific CD4+ T-cell Responses After an Acute Resolving Viral Infection: a Study of Parvovirus B19," Journal of Virology, 80(22):11209-11217, American Society For Microbiology, United States (Nov. 2006).
Khare, M., et al., "HLA Class Ii Transgenic Mice Authenticate Restriction of Myelin Oligodendrocyte Glycoprotein-specific Immune Response Implicated in Multiple Sclerosis Pathogenesis," International Immunology, 15(4):535-546, Oxford University Press, 1989, England (Apr. 2003).
Klebanoff, C.A., et al., "Therapeutic Cancer Vaccines: Are We There Yet?," Immunological reviews, 239(1):27-44, Blackwell, England (Jan. 2011).
Kumar, K.V.S.H., et al., "Twins and Endocrinology," Indian Journal of Endocrinology and Metabolism, 18(Suppl 1):S48-S52, Medknow Publications, India (Nov. 2014).
Lamb, J.R., et al., "Human T-Cell Clones Recognize Chemically Synthesized Peptides of Influenza Haemagglutinin," Nature, 300:66-69, Springer, United States (Nov. 1982).
Lewin, A., et al., "Effects of Substitutions in the CXXC Active-site Motif of the Extracytoplasmic Thioredoxin Resa," The Biochemical Journal, 414(1):81-91, Published by Portland Press on behalf of the Biochemical Society, England (Aug. 15, 2008).
Li, S.C., et al., "Twisting Immune Responses for Allogeneic Stem Cell Therapy," World Journal of Stem Cells, 1(1):30-35, Baishideng Publishing Group, United States (Dec. 31, 2009).
Lindqvist, C.A., et al., "Both CD4+ FoxP3+ and CD4+ FoxP3-T Cells From Patients With B-cell Malignancy Express Cytolytic Markers and Kill Autologous Leukaemic B Cells in Vitro," Immunology, 133(3):296-306, Blackwell Scientific Publications (Apr. 5, 2011).
Lodish, L., et al., "Molecular Cell Biology, 4th edition." W.H. Freeman & Co Ltd, New York, 2000, Section 6.3, Viruses: Structure, Function, and Uses, 1280 pages.
Louis, S., et al., "Contrasting CD25hiCD4+t Cells/foxp3 Patterns in Chronic Rejection and Operational Drug-free Tolerance," Transplantation, 81(3):398-407, Lippincott Williams & Wilkins (Feb. 15, 2006).
Lovitch, S.B., et al., "Amino-Terminal Flanking Residues Determine the Conformation of a Peptide-Class II MHC Complex," Journal of Immunology (Baltimore, Md. : 1950), 176(5):2958-2968, American Association of Immunologists, United States (Mar. 1, 2006).
Mach, B., et al., "Regulation of MHC Class II Genes: Lessons From a Disease," Annual Review of Immunology, 14:301-331, Annual Reviews Inc., c1983, United States (1996).
Maeda, M., et al., "CD1d-independent NKT Cells in Beta 2-microglobulin-deficient Mice Have Hybrid Phenotype and Function of Nk and T Cells," Journal of Immunology (Baltimore, Md. :

(56) References Cited

OTHER PUBLICATIONS

1950), 172(10):6115-6122, American Association of Immunologists, United States (May 15, 2004).

Maekawa, A., et al., "Evidence for a Domain-Swapped CD4 Dimer as the Coreceptor for Binding to Class II MHC," Journal of Immunology (Baltimore, Md. : 1950), 176(11):6873-6878, American Association of Immunologists (Jun. 1, 2006).

Markovicplese, S., et al., "T Cell Recognition of Immunodominant and Cryptic Proteolipid Protein Epitopes in Humans," Journal of Immunology (Baltimore, Md. : 1950), 155(2):982-992, American Association of Immunologists (Jul. 15, 1995).

Marti, M., et al., "Conformationally Correct Expression of Membrane-anchored Toxoplasma Gondii SAG1 in the Primitive Protozoan Giardia Duodenalis," Infection and Immunity, 70(2):1014-1016, American Society For Microbiology, United States (Feb. 2002).

Massilamany, C., et al., "Detection of Autoreactive CD4 T Cells Using Major Histocompatibility Complex Class II Dextramers," BMC Immunology, 12:40, BioMed Central, England (Jul. 2011).

Matsuda, J.L., et al., "CD1d-restricted INKT Cells, the 'Swiss-Army Knife' of the Immune System," Current Opinion in Immunology, 20(3):358-368, Elsevier, England (Jun. 2008).

Matthiasx, L.J., et al., "Disulfide Exchange in Domain 2 of CD4 is Required for Entry of HIV-1," Nature Immunology, 3(8):727-732, Nature America Inc. c2000, United States (Aug. 2002).

Maynard, C.L., et al., "Regulatory T Cells Expressing Interleukin 10 Develop From Foxp3+ and Foxp3-Precursor Cells in the Absence of Interleukin 10," Nature Immunology, 8(9):931-941, Nature America Inc. c2000, United States (Sep. 2007).

MedlinePlus Medical Dictionary (Merriam Webster, Inc., 2017).

Merkler, D., et al., "Myelin Oligodendrocyte Glycoprotein-induced Experimental Autoimmune Encephalomyelitis in the Common Marmoset Reflects the Immunopathology of Pattern II Multiple Sclerosis Lesions," Multiple Sclerosis (Houndmills, Basingstoke, England), 12(4):369-374, SAGE Publications, England (Aug. 2006).

Moldovan, M.C., et al., "CD4 Dimers Constitute the Functional Component Required for T Cell Activation," Journal of Immunology (Baltimore, Md. : 1950), 169(11):6261-6268, American Association of Immunologists (Dec. 1, 2002).

Nepom, G.T., "MHC Class II Tetramers," The Journal of Immunology, 188(6):2477-2482, American Association of Immunologists, United States (Mar. 2012).

NetMHCIIpan Server—Prediction Results dated Sep. 26, 2018, 1 page.

Nielsen, M., et al., "Quantitative Predictions of Peptide Binding to Any HLA-DR Molecule of Known Sequence: NetMHCIIpan," PLoS computational biology, 4(7):e1000107, Public Library of Science, [2005], United States (Jul. 4, 2008).

Non-Final Office Action dated Apr. 1, 2014, in U.S. Appl. No. 12/735,740, Saint-Remy, J.M., filed Aug. 13, 2010, 12 Pages.

Non-Final Office Action dated Apr. 20, 2015, in U.S. Appl. No. 12/377,048, Saint-Remy, J.M., filed Feb. 10, 2009, 15 Pages.

Non-Final Office Action dated Aug. 14, 2019, in U.S. Appl. No. 15/151,868, Saint-Remy, J.M., et al., filed May 11, 2016, 15 Pages.

Non-Final Office Action dated Aug. 17, 2016, in U.S. Appl. No. 14/589,134, Saint-Remy, J.M., filed Jan. 5, 2015, 11 Pages.

Non-Final Office Action dated Aug. 24, 2017, in U.S. Appl. No. 14/450,722, Saint-Remy, J.M., filed Aug. 4, 2014, 9 Pages.

Non-Final Office Action dated Dec. 1, 2017, in U.S. Appl. No. 14/980,932, Saint-Remy, J.M., filed Dec. 28, 2015.

Non-Final Office Action dated Feb. 20, 2018, in U.S. Appl. No. 14/976,259, Saint-Remy, J.M., filed Dec. 21, 2015, 17 Pages.

Non-Final Office Action dated Feb. 23, 2017, in U.S. Appl. No. 14/375,324, Saint-Remy, J.M., filed Jul. 29, 2014, 12 Pages.

Non-Final Office Action dated Jan. 11, 2016, in U.S. Appl. No. 12/735,739, Saint-Remy, J.M., filed Aug. 13, 2010, 11 Pages.

Non-Final Office Action dated Jan. 14, 2019, in U.S. Appl. No. 14/450,722, Saint-Remy, J.M., filed Aug. 4, 2014, 8 Pages.

Non-Final Office Action dated Jan. 18, 2013, in U.S. Appl. No. 12/735,742, Saint-Remy, J.M., filed Aug. 13, 2010, 27 Pages.

Non-Final Office Action dated Jan. 22, 2013, in U.S. Appl. No. 12/735,740, Saint-Remy, J.M., filed Aug. 13, 2010, 21 Pages.

Non-Final Office Action dated Jan. 9, 2014, in U.S. Appl. No. 12/735,744, Saint-Remy, J.M., filed Aug. 13, 2010, 10 Pages.

Non-Final Office Action dated Jul. 11, 2013, in U.S. Appl. No. 12/735,739, Saint-Remy, J.M., filed Aug. 13, 2010, 8 Pages.

Non-Final Office Action dated Jul. 14, 2017, in U.S. Appl. No. 14/589,134, Saint-Remy, J.M., filed Jan. 5, 2015, 16 Pages.

Non-Final Office Action dated Jun. 17, 2016, in U.S. Appl. No. 13/988,925, Saint-Remy, J.M., filed Jun. 6, 2013, 9 Pages.

Non-Final Office Action dated Jun. 25, 2018, in U.S. Appl. No. 14/375,324, Saint-Remy, J.M., filed Jul. 29, 2014, 10 Pages.

Non-Final Office Action dated Jun. 8, 2018, in U.S. Appl. No. 15/151,868, Saint-Remy, J.M., et al., filed May 11, 2016, 12 Pages.

Non-Final Office Action dated May 17, 2019, in U.S. Appl. No. 14/976,259, Saint-Remy, J.M., filed Dec. 21, 2015, 15 Pages.

Non-Final Office Action dated Nov. 25, 2014, in U.S. Appl. No. 12/735,744, Saint-Remy, J.M., filed Aug. 13, 2010, 10 Pages.

Non-Final Office Action dated Nov. 9, 2017, in U.S. Appl. No. 13/988,925, Saint-Remy, J.M., filed Jun. 6, 2013, 8 Pages.

Non-Final Office Action dated Oct. 2, 2019, in U.S. Appl. No. 14/375,324, Saint-Remy, J.M., filed Jul. 29, 2014, 10 Pages.

Non-Final Office Action dated Oct. 2, 2018, in U.S. Appl. No. 15/388,398, Saint-Remy, J.M., filed Dec. 22, 2016, 17 Pages.

Non-Final Office Action dated Oct. 5, 2018, in U.S. Appl. No. 14/589,134, Saint-Remy, J.M., filed Jan. 5, 2015, 6 Pages.

Non-Final Office Action dated Sep. 11, 2018, in U.S. Appl. No. 14/980,932, Saint-Remy, J.M., filed Dec. 28, 2015,.

Non-Final Office Action dated Sep. 18, 2018, in U.S. Appl. No. 15/516,045, Saint-Remy, J.M., et al., filed Mar. 31, 2017, 7 Pages.

Non-Final Office Action dated Sep. 7, 2018, in U.S. Appl. No. 14/894,221, Saint-Remy, J.M., et al., filed Nov. 25, 2015, 7 Pages.

Notice of Allowance dated Apr. 15, 2019, in U.S. Appl. No. 14/894,221, Saint-Remy, J.M., et al., filed Nov. 25, 2015, 8 Pages.

Notice of Allowance dated Apr. 3, 2019, in U.S. Appl. No. 14/980,932, Saint-Remy, J.M., filed Dec. 28, 2015.

Notice of Allowance dated Feb. 21, 2019, in U.S. Appl. No. 14/589,134, Saint-Remy, J.M., filed Jan. 5, 2015, 10 Pages.

Notice of Allowance dated Mar. 26, 2018, in U.S. Appl. No. 13/988,925, Saint-Remy, J.M., filed Jun. 6, 2013, 8 Pages.

Notice of Allowance dated Mar. 3, 2015, in U.S. Appl. No. 12/735,740, Saint-Remy, J.M., filed Aug. 13, 2010, 2 Pages.

Notice of Allowance dated Oct. 2, 2014, in U.S. Appl. No. 12/735,740, Saint-Remy, J.M., filed Aug. 13, 2010, 7 Pages.

Notice of Allowance dated Sep. 22, 2015, in U.S. Appl. No. 12/377,048, Saint-Remy, J.M., filed Feb. 10, 2009, 9 Pages.

Notice of Allowance dated Sep. 27, 2019, in U.S. Appl. No. 15/388,398, Saint-Remy, J.M., filed Dec. 22, 2016, 11 Pages.

Notice of Allowance dated Sep. 28, 2015, in U.S. Appl. No. 12/735,744, Saint-Remy, J.M., filed Aug. 13, 2010, 7 Pages.

Ochoa-Garay, J., et al., "The Ability of Peptides to Induce Cytotoxic T Cells in Vitro Does Not Strongly Correlate With Their Affinity for the H-2ld Molecule: Implications for Vaccine Design and Immunotherapy," Molecular Immunology, 34(3):273-281, Pergamon Press, England (Feb. 1997).

Okubo, M., et al., "Analysis of HLA-DRB1*0901-Binding HPV-16 E7 Helper T Cell Epitope.," The Journal of Obstetrics and Gynaecology Research, 30(2):120-129, Wiley, Australia (Apr. 2004).

Oliveira, M.A., et al., "Insights into the Specificity of Thioredoxin Reductase-Thioredoxin Interactions. A Structural and Functional Investigation of the Yeast Thioredoxin System," Biochemistry, 49(15):3317-3326, American Chemical Society, United States (Apr. 2010).

O'Sullivan, D.M., et al., "MHC HLA-DR Gamma Chain, Partial [*Homo sapiens*]," GenBank AAA58655.1, 1994, p. 1.

Papanastasiou, P., et al., "Primary Structure and Biochemical Properties of a Variant-specific Surface Protein of Giardia.," Molecular and Biochemical Parasitology, 86(1):13-27, Elsevier/North-Holland Biomedical Press, Netherlands (May 1997).

Park, B., et al., "Redox Regulation Facilitates Optimal Peptide Selection by MHC Class I During Antigen Processing," Cell, 127(2):369-382, Cell Press, United States (Oct. 2006).

(56) References Cited

OTHER PUBLICATIONS

Peterson, R.A., "Regulatory T-cells: Diverse Phenotypes Integral to Immune Homeostasis and Suppression," Toxicologic Pathology, 40(2):186-204, Sage Publications, United States (2012).

Pillai, A.B., "Host NKT Cells Can Prevent Graft-versus-host Disease and Permit Graft Antitumor Activity After Bone Marrow Transplantation," Journal of Immunology, 178(10):6242-6251, American Association of Immunologists, United States (2007).

Pira, L.G., et al., "High Throughput T Epitope Mapping and Vaccine Development," Journal of Biomedicine & Biotechnology, 2010:12, Hindawi Pub. Corp, United States (Jun. 15, 2010).

Qin, W., et al., "Fusion Protein of CDR Mimetic Peptide With Fc Inhibit TNF-alpha Induced Cytotoxicity.," Molecular Immunology, 43(6):660-666, Pergamon Press, England (Feb. 2006).

Quintana, F, J., et al., "Epitope Spreading as an Early Pathogenic Event in Pediatric Multiple Sclerosis," Neurology, 83(24):2219-2226, Lippincott Williams & Wilkins, United States (Dec. 2014).

Racaniello, V., "How Many Viruses on Earth?," Virology Blog, 2013, 3 pages. Retrieved from Internet:[URL:http://www.virology.ws/2013/09/06/how-many-viruses-on-earth/].

Rammensee, H.G., et al., "MHC Ligands and Peptide Motifs," in Molecular Biology Intelligence Unit, p. 317, Springer, New York & Austin, Texas, USA (1997).

Reznik, S.I., et al., "Indirect Allorecognition of Mismatched Donor Hla Class Ii Peptides in Lung Transplant Recipients With Bronchiolitis Obliterans Syndrome," American Journal of Transplantation, 1(3):228-235, Wiley-Blackwell, United States (Sep. 2001).

Robinson, A.P., et al., "Vaccine Protocol," in Methods in Molecular Medicine, Humana Press, Totowa, NJ, Ed. Andrew Robinson, Michael J. Hudson and Martin P. Cranage, pp. 121-123 (2003).

Roep, B.O., et al., "The Problems and Promises of Research Into Human Immunology and Autoimmune Disease," Nature Medicine, 18(1):48-53, Nature Publishing Company, United States (Jan. 2012).

Roopenian, D., et al., "The Immunogenomics of Minor Histocompatibility Antigens.," Immunological Reviews, 190:86-94, Blackwell, England (Dec. 2002).

Roper, R.L., et al., "SARS Vaccines: Where Are We?," Expert Review of Vaccines, 8(7):887-898, Taylor & Francis, England (Jul. 2009).

Saez-Borderias, A., et al., "Expression and Function of NKG2D in CD4+ T cells Specific for Human Cytomegalovirus," European Journal of Immunology, 36(12):3198-3206, Wiley-VCH, Germany (Dec. 2006).

Santin, A, D, et al., "Human Papillomavirus Type 16 and 18 E7-Pulsed Dendritic Cell Vaccination of Stage IB or IIA Cervical Cancer Patients: A Phase I Escalating-Dose Trial," Journal of Virology, 82(4):1968-1979, American Society for Microbiology, United States (Feb. 2008).

Savoldo, B, et al., "Generation of EBV-specific CD4+ Cytotoxic T cells from Virus Naive Individuals," Journal of Immunology, 168(2):909-918, American Association of Immunologists, United States (Jan. 2002).

Schrieber, T.H., et al., "Tumor Immunogenicity and Responsiveness to Cancer Vaccine Therapy: the State of the Art," Seminars in Immunology, 22(3):105-112, Academic Press, Academic Press (Jun. 2010).

Schultz, E.S., et al., "A MAGE-A3 Peptide Presented by HLA-DP4 Is Recognized on Tumor Cells by CD4+ Cytolytic T Lymphocyte," Cancer Research, 60(22):6272-6275, American Association for Cancer Research, United States (Nov. 2000).

Schwartz, R.H., et al., "The T Lymphocyte Response to Cytochrome c. V. Determination of the Minimal Peptide Size Required for Stimulation of T Cell Clones and Assessment of the Contribution of Each Residue Beyond This Size to Antigenic Potency," Journal of Immunology, 135(4):2598-2608, American Association of Immunologists, United States (Oct. 1985).

Sette, A and Fikes, J., "Epitope-based Vaccines: an Update on Epitope Identification, Vaccine Design and Delivery," Current Opinion in Immunology, 15(4):461-470, Elsevier, England (Aug. 2003).

Sette, A and Sidney, J., "HLA Supertypes and Supermotifs: a Functional Perspective on HLA Polymorphism," Current Opinion in Immunology, 10(4):478-482, Elsevier, England (Aug. 1998).

Shi, J and Bhattacharyya, M. K., "A Novel Plasma Membrane-bound Thioredoxin From Soybean," Plant Molecular Biology, 32(4):653-662, Kluwer Academic, Netherlands (Nov. 1996).

Skonier, J., et al., "Human Transforming Growth Factor-beta Induced Gene Product (BIGH3) mRNA, Complete cds," GenBank M77349.1, Jan. 14, 1995, 3 pages.

Stenstrom, M., et al., "Natural Killer T-cell Populations in C57BL/6 and NK1.1 Congenic BALB.NK Mice—a Novel Thymic Subset defined in BALB.NK Mice.," Immunology, 114(3):336-345, Blackwell Scientific Publications, England (Mar. 2005).

Straub, R. B., et al., "Allelic Variation in GAD1 (GAD67) is Associated With Schizophrenia and Influences Cortical Function and Gene Expression," Molecular Psychiatry, 12(9):854-869, Nature Publishing Group Specialist Journals, England (Sep. 2007).

Sundar, S.K and Menezes, J., "Generation of Epstein-bar Virus Antigen-specific Suppressor T Cells in Vitro," International Journal of Cancer, 35(3):351-357, Wiley-Liss, United States (Mar. 1985).

Taylor, A., et al., "T Regulatory Cells and Allergy," Microbes and Infection, 7(7-8):1049-1055, Elsevier, France (Jun. 2005).

Texier, C., et al., "On the Diversity and Heterogeneity of H-2(D)-restricted Determinants and T Cell Epitopes From the Major Bee Venom Allergen," International Immunology, 11(8):1313-1326, Oxford, England (Aug. 1999).

Thomson, S.A., et al., "Targeting a Polyepitope Protein Incorporating Multiple Class 11-restricted Viral Epitopes to the Secretory/endocytic Pathway Facilitates Immune Recognition by CD4+ Cytotoxic T Lymphocytes: a Novel Approach to Vaccine Design," Journal of Virology, 72(3):2246-2252, American Society For Microbiology, United States (Mar. 1998).

Tindle, R.W., et al., "A "Public" T-helper Epitope of the E7 Transforming Protein of Human Papillomavirus 16 Provides Cognate Help for Several E7 B-cell Epitopes From Cervical Cancer-associated Human Papillomavirus Genotypes," Proceedings of the National Academy of Sciences of the United States of America, 88(13):5887-5891, National Academy of Sciences, United States (Jul. 1991).

Tisch, R and McDevitt, H.O., "Antigen-specific Immunotherapy: is It a Real Possibility to Combat T-cell-mediated Autoimmunity?," Proceedings of the National Academy of Sciences of the United States of America, 91(2):437-438, National Academy of Sciences, United States (Jan. 1994).

Toyokawa, H., et al., "Relative Contribution of Direct and Indirect Allorecognition in Developing Tolerance After Liver Transplantation," Liver Transplantation, 14(3):346-357, Wiley, United States (Mar. 2008).

Tsuji, N.M., et al., "Antigen-specific, CD4+CD25+ Regulatory T Cell Clones Induced in Peyer's Patches," International Immunology, 15(4):525-534, Oxford, England (Apr. 2003).

U.S. Appl. No. 16/091,549, unpublished application, filed Oct. 5, 2018.

UniProt 015523.2, 2017, pp. 1-7.

UniProt P01906.2, 2017, p. 1-6.

Vignali, D.A. and Strominger, J.L., "Amino Acid Residues That Flank Core Peptide Epitopes and the Extracellular Domains of CD4 Modulate Differential Signaling Through the T Cell Receptor," The Journal of Experimental Medicine, 179(6):1945-1956, Rockefeller University Press, United States (Jun. 1994).

Voo, K.S., et al., "Functional Characterization of Ebv-encoded Nuclear Antigen 1-specific CD4+ Helper and Regulatory T Cells Elicited by in Vitro Peptide Stimulation," Cancer Research, 65(4):1577-1586, American Association for Cancer Research, United States (Feb. 2006).

Wang et al., "Generation and characterization of HLA-A*2.1 restricted and Prostein 31-39 specific NKT cell lines," Acta Academiae Medicine Militaris Tertiae, 28(16):1652-1655 (2006) (English language translation provided) (11 pages).

Wang, R.F., "Immune Suppression by Tumor-specific CD4+ Regulatory T-cells in Cancer," Seminars in Cancer Biology, 16(1):73-79, Academic Press, England (Feb. 2006).

(56) References Cited

OTHER PUBLICATIONS

Weissert, R., et al., "MHC Class Ii-regulated Central Nervous System Autoaggression and T Cell Responses in Peripheral Lymphoid Tissues Are Dissociated in Myelin Oligodendrocyte Glycoprotein-induced Experimental Autoimmune Encephalomyelitis.," Journal of Immunology, 166(12):7588-7599, American Association of Immunologists, United States (Jun. 2001).
Wekerle, H., et al., "Autoimmunity's Next Top Models," Nature Medicine, 18(1):66-70, Nature Publishing Company, United States (Jan. 2012).
Wiker, H.G., et al., "Cloning, Expression and Significance of MPT53 for Identification of Secreted Proteins of Mycobacterium Tuberculosis," Microbial Pathogenesis, 26(4):207-219, Academic Press, England (Apr. 1999).
Witmer, C. and Young, G., "Factor VIII Inhibitors in Hemophilia a: Rationale and Latest Evidence," Therapeutic Advances in Hematology, 4(1):59-72, Sage, England (Feb. 2013).
Wobus, A.M and Boheler, K.R., "Embryonic Stem Cells: Prospects for Developmental Biology and Cell Therapy," Physiological Reviews, 85(2):635-678, American Physiological Society, United States (Apr. 2005).
Wood, K.J and Sakaguchi, S., "Regulatory T Cells in Transplantation Tolerance," Nature Reviews. Immunology, 3(3):199-210, Nature Pub. Group, England (Mar. 2003).
Wooldridge, L., et al., "Tricks With Tetramers: How to Get the Most From Multimeric Peptide-MHC," Immunology, 126(2):147-164, Blackwell Scientific Publications, England (Feb. 2009).
Written Description Training Materials, Revision 1, Mar. 25, 2008, United States Patent and Trademark Office.
Written Opinion for International Application No. PCT/EP2007/007165, European Patent Office, Netherlands, dated Jan. 17, 2008, 8 Pages.
Written Opinion for International Application No. PCT/EP2009/051804, European Patent Office, Netherlands, dated Aug. 11, 2009, 8 Pages.
Written Opinion for International Application No. PCT/EP2009/051807, European Patent Office, Netherlands, dated Jul. 13, 2009, 5 Pages.
Written Opinion for International Application No. PCT/EP2009/051808, European Patent Office, Netherlands, dated Feb. 18, 2010, 7 Pages.
Written Opinion for International Application No. PCT/EP2014/060994, European Patent Office, Netherlands, dated Jun. 1, 2015, 7 pages.
Written Opinion for International Application No. PCT/EP2014/060994, European Patent Office, Netherlands, dated Sep. 18, 2014, 6 pages.
Written Opinion of the International Preliminary Examining Authority for International Application No. PCT/BE2013/000006, European Patent Office, Germany, dated May 24, 2014, 17 Pages.
Written Opinion of the International Searching Authority for International Application No. PCT/BE2008/000010, European Patent Office, Germany, dated Jul. 2, 2008, 8 Pages.
Written Opinion of the International Searching Authority for International Application No. PCT/BE2013/000006, European Patent Office, Germany, dated Feb. 14, 2014, 10 Pages.
Written Opinion of the International Searching Authority for International Application No. PCT/EP2009/051806, European Patent Office, Netherlands, dated Aug. 11, 2009, 7 Pages.
Wu, T.C., et al., "Engineering an Intracellular Pathway for Major Histocompatibility Complex Class II Presentation of Antigens," Proceedings of the National Academy of Sciences of the United States of America, 92(25):11671-11675, National Academy of Sciences, United States (Dec. 1995).
Zeng, Z., et al., "Crystal Structure of Mouse CD1: an MHC-like Fold With a Large Hydrophobic Binding Groove," Science, 277(5324):339-345, American Association for the Advancement of Science, United States (Jul. 1997).
Zhang, D., et al., "Preclinical Experimental Models of Drug Metabolism and Disposition in Drug Discovery and Development," Acta Pharmaceutica Sinica B, 2(6):549-561, (Dec. 2012).
Zhang, Y., et al., "A Mage-3 Peptide Presented by HLA-DR1 to CD4+ T Cells That Were Isolated From a Melanoma Patient Vaccinated With a Mage-3 Protein," Journal of Immunology, 171(1):219-225, American Association of Immunologists, United States (Jul. 2003).
Zhao, D.M., et al., "Activated CD4+CD25+ T Cells Selectively Kill B Lymphocytes," Blood, 107(10):3925-3932, American Society of Hematology, United States (May 2006).
Non-Final Office Action dated Jan. 20, 2012, in U.S. Appl. No. 12/735,754, Saint-Remy, J.M., filed Aug. 13, 2010, 16 Pages.
Final Office Action dated Sep. 26, 2012, in U.S. Appl. No. 12/735,754, Saint-Remy, J.M., filed Aug. 13, 2010, 18 Pages.
Non-Final Office Action dated Jul. 24, 2014, in U.S. Appl. No. 12/735,754, Saint-Remy, J.M., filed Aug. 13, 2010, 13 Pages.
Notice of Allowance dated Jan. 30, 2015, in U.S. Appl. No. 12/735,754, Saint-Remy, J.M., filed Aug. 13, 2010, 9 Pages.
Advisory Action dated Apr. 9, 2013, in U.S. Appl. No. 12/735,754, Saint-Remy, J.M., filed Aug. 13, 2010, 3 Pages.
Non-Final Office Action dated Sep. 7, 2016, in U.S. Appl. No. 14/686,855, Saint-Remy, J.M., filed Apr. 15, 2015, 9 Pages.
Final Office Action dated Mar. 23, 2017, in U.S. Appl. No. 14/686,855, Saint-Remy, J.M., filed Apr. 15, 2015, 11 Pages.
Advisory Action dated Jul. 3, 2017, in U.S. Appl. No. 14/686,855, Saint-Remy, J.M., filed Apr. 15, 2015, 3 Pages.
Notice of Allowance dated September/, 201/, in U.S. Appl. No. 14/686,855, Saint-Remy, J.M., filed Apr. 15, 2015, 11 Pages.
Written Opinion for International Application No. PCT/EP2009/051803, European Patent Office, Netherlands, dated Aug. 2010, 7 Pages.
Final Office Action dated Nov. 5, 2019, in U.S. Appl. No. 14/450,/22, Saint-Remy, J.M., filed Aug. 4, 2014, 8 Pages.
Molecular Cell Biology (2000, W.H.Freeman and Company, 4th Ed.) (Year: 2000).
Racaniello, V. (Virology Blog, 2013) (Year: 2013).
ViralZone (2017) (Year: 2017).
DermNet Nz (2019) (Year: 2019).

\* cited by examiner

SEQUENCE LISTING

```
<160> NUMBER OF SEQ ID NOS: 22

<210> SEQ ID NO 1
<211> LENGTH: 16
<212> TYPE: PRT
<213> ORGANISM: Artificial Sequence
<220> FEATURE:
<223> OTHER INFORMATION: redox motif + MOG epitope

<400> SEQUENCE: 1

Cys Gly Pro Cys Ser Arg Val Val His Leu Tyr Arg Asn Gly Lys Asp
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: MOG epitope

<400> SEQUENCE: 2

Ser Arg Val Val His Leu Tyr Arg Asn Gly Lys Asp
1               5                   10

<210> SEQ ID NO 3
<211> LENGTH: 19
<212> TYPE: PRT
<213> ORGANISM: Artificial Sequence
<220> FEATURE:
<223> OTHER INFORMATION: redox motif + influenza hemaglutinin epitope

<400> SEQUENCE: 3

Cys Gly His Cys Lys Tyr Val Lys Gln Asn Thr Leu Lys His Glu Met
1               5                   10                  15

Ala Gly Gly

<210> SEQ ID NO 4
<211> LENGTH: 15
<212> TYPE: PRT
<213> ORGANISM: Artificial Sequence
<220> FEATURE:
<223> OTHER INFORMATION: influenza hemaglutinin epitope
```

```
<400> SEQUENCE: 4

Lys Tyr Val Lys Gln Asn Thr Leu Lys His Glu Met Ala Gly Gly
1               5                  10                  15

<210> SEQ ID NO 5
<211> LENGTH: 13
<212> TYPE: PRT
<213> ORGANISM: Artificial Sequence
<220> FEATURE:
<223> OTHER INFORMATION: Redox motif  + Dby epitope

<400> SEQUENCE: 5

Cys His Gly Cys Phe Asn Ser Asn Arg Ala Asn Ser Ser
1               5                  10

<210> SEQ ID NO 6
<211> LENGTH: 9
<212> TYPE: PRT
<213> ORGANISM: Artificial Sequence
<220> FEATURE:
<223> OTHER INFORMATION: Dby epitope

<400> SEQUENCE: 6

Phe Asn Ser Asn Arg Ala Asn Ser Ser
1               5

<210> SEQ ID NO 7
<211> LENGTH: 15
<212> TYPE: PRT
<213> ORGANISM: Artificial Sequence
<220> FEATURE:
<223> OTHER INFORMATION: redox motif + GAD65 epitope

<400> SEQUENCE: 7

Cys Arg Leu Cys Lys Val Ala Pro Val Ile Lys Ala Arg Met Met
1               5                  10                  15

<210> SEQ ID NO 8
<211> LENGTH: 11
<212> TYPE: PRT
<213> ORGANISM: Artificial Sequence
<220> FEATURE:
<223> OTHER INFORMATION: GAD65 epitope

<400> SEQUENCE: 8

Lys Val Ala Pro Val Ile Lys Ala Arg Met Met
1               5                  10

<210> SEQ ID NO 9
<211> LENGTH: 20
<212> TYPE: PRT
<213> ORGANISM: Artificial Sequence
<220> FEATURE:
<223> OTHER INFORMATION: redox motif + glycine linker+ insulin epitope

<400> SEQUENCE: 9

Cys Gly His Cys Gly Ser His Leu Val Glu Ala Leu Tyr Leu Val Cys
1               5                  10                  15

Gly Glu Arg Gly
            20

<210> SEQ ID NO 10
<211> LENGTH: 15
<212> TYPE: PRT
<213> ORGANISM: Artificial Sequence
<220> FEATURE:
```

-continued

<223> OTHER INFORMATION: insulin epitope

<400> SEQUENCE: 10

Ser His Leu Val Glu Ala Leu Tyr Leu Val Cys Gly Glu Arg Gly
1               5                   10                  15

<210> SEQ ID NO 11
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (1)..(1)
<223> OTHER INFORMATION: Xaa can be Cys, Ser, or Thr
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 11

Xaa Xaa Xaa Cys
1

<210> SEQ ID NO 12
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be Cys, Ser, or Thr

<400> SEQUENCE: 12

Cys Xaa Xaa Xaa
1

<210> SEQ ID NO 13
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 13

Cys Xaa Xaa Cys
1

<210> SEQ ID NO 14
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 14

```
Cys Xaa Xaa Ser
1

<210> SEQ ID NO 15
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 15

Cys Xaa Xaa Thr
1

<210> SEQ ID NO 16
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 16

Ser Xaa Xaa Cys
1

<210> SEQ ID NO 17
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 17

Thr Xaa Xaa Cys
1

<210> SEQ ID NO 18
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Cys, or Ser

<400> SEQUENCE: 18

Cys Xaa Xaa Xaa
1

<210> SEQ ID NO 19
<211> LENGTH: 4
```

```
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (1)..(1)
<223> OTHER INFORMATION: Xaa can be Cys, or Ser
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 19

Xaa Xaa Xaa Cys
1

<210> SEQ ID NO 20
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (1)..(1)
<223> OTHER INFORMATION: Xaa can be Cys, Ser, or Thr
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Cys, Ser, or Thr

<400> SEQUENCE: 20

Xaa Xaa Xaa Xaa
1

<210> SEQ ID NO 21
<211> LENGTH: 14
<212> TYPE: PRT
<213> ORGANISM: Artificial Sequence
<220> FEATURE:
<223> OTHER INFORMATION: redox motif repeat
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(13)
<223> OTHER INFORMATION: Xaa can be any naturally occurring amino acid

<400> SEQUENCE: 21

Cys Xaa Xaa Cys Xaa Cys Xaa Xaa Cys Xaa Cys Xaa Xaa Cys
1               5                   10

<210> SEQ ID NO 22
<211> LENGTH: 10
```

```
<212> TYPE: PRT
<213> ORGANISM: Artificial Sequence
<220> FEATURE:
<223> OTHER INFORMATION: motif repeat
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid

<400> SEQUENCE: 22

Cys Xaa Xaa Cys Xaa Xaa Cys Xaa Xaa Cys
1               5                   10
```

METHOD FOR THE DETECTION, PREPARATION AND DEPLETION OF CD4+ T LYMPHOCYTES

CROSS-REFERENCE TO RELATED APPLICATIONS

This application is the continuation of U.S. patent application Ser. No. 14/894,221, filed 25 Nov. 2015, which is the U.S. national phase of International Application No. PCT/EP2014/060994 filed 27 May 2014, which designated the U.S. and claims priority to GB Patent Application No. 1309469.3 filed 28 May 2013, the entire contents of each of which are hereby incorporated by reference.

REFERENCE TO SEQUENCE LISTING SUBMITTED ELECTRONICALLY

The content of the electronically submitted sequence listing (Name: 2752_0115_sequence_listing.txt; Size: 7,042 bytes; and Date of Creation: Jul. 9, 2019) filed with the application is incorporated herein by reference in its entirety.

FIELD OF THE INVENTION

The present invention relates to synthetic peptides encompassing class II-restricted major histocompatibility complex (MHC) T cell epitopes containing a thioredox motif within flanking residues for the detection, preparation or depletion of CD4+ T lymphocytes in or from body fluids or culture medium.

BACKGROUND OF THE INVENTION

Lymphocytes play a central role in the elaboration of immune responses against foreign antigens and in the control of diseases. Such recruitment and activation of lymphocytes can be beneficial as in responses against infectious agents, or detrimental, such as exemplified by auto-immune diseases, responses to allergens and in graft rejection. There are therefore a large number of circumstances in which it would be advantageous to detect, enumerate, purify or deplete such lymphocytes. Current methods to achieve these goals are, however, unsatisfactory.

Lymphocytes are divided in several lineages and subsets according to the presence of surface molecule and function. Lymphocytes of the CD4 lineage are characterized by the presence of the CD4 molecule, a co-receptor associated with the antigen-specific T cell receptor (called CD3).

CD4+ T cells recognize antigens after their processing by antigen-presenting cells and presentation by class II major histocompatibility complexes (MHC class II). This results in the formation of an immune synapse through assembly of MHC class II determinants, antigen-derived peptides and the antigen-specific T cell receptor (TCR), a molecular complex which is stabilized by recruitment of the CD4+ molecule.

However, the recognition of a peptide-MHC class II complex by a TCR is of low affinity, namely several orders of magnitude lower than for the binding of an antibody to its epitope. This is due to the fact that the TCR contacts a linear sequence made of 9 amino acid residues bound to class II MHC cleft, together with residues pertaining to the MHC molecule itself, as opposed to the large area made by antibody and epitope binding. TCR low affinity results in inefficient detection, in particular in complex body fluids.

This has led to the development of methods in which peptide-MHC complexes are reconstituted using a soluble form of MHC. Usually, soluble MHC molecules are multimerized in the form of dimers, tetramers or pentamers. Numerous variants of these multimers have recently been described (Davis et al. (2011) Nature Rev. Immunol. 11, 551-558. However, although both the specificity and sensitivity of these multimers have been significantly increased, these detection tools still remain relatively inefficient under circumstances of low T cell frequency or when TCR affinity is a limiting factor, such as for T cells in naïve configuration.

MHC class II multimers for detecting T cell epitopes are reviewed in for example Nepom (2012) J. Immunol. 188, 2477-2482. This review also points to the limited affinity of MHC class II multimers for CD4+ cells, and the use of citrinullated amino acids to improve this affinity Wooldridge et al. (2009) Immunology 126, 147-164 discuss peptide-MHC complexes and the low affinity of epitope MHC complexes. An attempt to increase T cell epitope binding with MHC class II complexes, by introducing hydrophobic amino acids adjacent to the epitope sequence is described in WO97040852.

WO2008017517 describes peptides with a T cell epitope and a reductase motif sequence in the generation of a cytolytic T cell population. Carlier et al. (2012) PloS ONE 7(10), e45366, 1-14 disclose that the synapse formed between the MHC-peptide complex and cognate TCR is stabilized by this type of peptides. The experimental results herein demonstrate that the number and the duration of dimer formation between antigen presenting cells and CD4+ T cells increases when peptides are used which comprises a T cell epitope sequence and a redox motif sequence.

The contrast between the increasing need for methods to detect CD4+ T cells in areas as diverse as auto-immune diseases, cancer or evaluation of responses towards vaccination, to cite just a few, and the poor efficiency of available methods makes it an urgent need to improve such methods

SUMMARY OF THE INVENTION

The first aspect of the invention relates to in vitro methods for detecting class II restricted CD4+ T cells in a sample. These methods comprise the steps of:
  providing a sample,
  contacting the sample with an isolated complex of an MHC class II molecule and a peptide, the peptide comprising an MHC class II restricted T cell epitope of an antigenic protein and immediately adjacent thereof, or separated by a linker of at most 7 amino acids a sequence with a [CST]-xx-C [SEQ ID NO:11] or C-xx-[CST] [SEQ ID NO:12] motif,
  detecting CD4+ T cells by measuring the binding of the complex with cells in the sample, wherein the binding of the complex to a cell is indicative for the presence of CD4+ T cells in the sample.

In specific embodiments the motif is CxxC [SEQ ID NO:13].

In specific embodiments the linker has a length of maximum 4 amino acids.

In other embodiments the peptide occurs in a non-covalent complex with the MHC class II molecule and has a length of between 12 and 20 amino acids.

The sample can be a blood sample, a tissue sample, such as synovial fluid from rheumatoid arthritis patients, pleural fluid of e.g. patients with infectious pneumonia or tuberculosis.

A sample can comprise different types of CD4+ T cells. The CD4+ T cells to be detected in the sample can be one or more of naïve CD4+ T cells, antigen-exposed CD4+ T cells, Tregs, induced Tregs, CD4+ T cells obtained during therapy or during vaccination, or CD4+ T cells in tissues.

In particular embodiments, the complex is a fusion protein of the peptide and an MCH class II molecule.

In particular embodiments the MHC Class II molecule is present in a cell lysate, or in a purified fraction of the cell lysate. The MHC molecule can be obtained by recombinant expression.

Typically the epitope sequence in the peptide is identical to the sequence in the antigen. Alternatively, the MHC class II anchoring residues are modified compared to the epitope as occurring in the antigen to modulate the binding affinity of the peptide to the CD4+ T cells.

Different variations of complexes are envisaged such as MHC molecules in the complex as tetramers, dextramers, soluble complexes, complexes attached to an insoluble carrier or a substrate.

Embodiments of the methods of the invention further comprise the step of isolating the CD4+ T cells bound to the complex.

Embodiments of the methods of the invention further comprise the step of detecting or isolating subpopulations of detected CD4+ T cells.

Embodiments of the methods of the invention further comprising the step of detecting or isolating subpopulations of isolated CD4+ T cells.

Another aspect of the present invention relates to a composition comprising a an isolated complex of:

An MCH class II molecule and a peptide comprising an MHC class II restricted T cell epitope of an antigenic protein and immediately adjacent thereof, or separated by a linker of at most 7 amino acids a sequence with a [CST]-xx-C [SEQ ID NO:11] or C-xx-[CST] [SEQ ID NO:12] motif In typical embodiments the motif is CxxC [SEQ ID NO:13]. In other typical embodiments the linker has a length of at most 4 amino acids.

The complex between the peptide and the MHC molecule can be a non-covalently bound complex or can be a covalently bound complex.

The complex can also be a fusion protein of an MHC class II protein with said peptide. In typical embodiments, wherein the peptide occurs in a non-covalent complex or in a covalent complex, other than a fusion protein, the peptide has a length of between 12 and 20 amino acids.

The complex can be attached to a carrier, such as a bead or a plate.

A further aspect of the invention relates to the use of a peptide comprising a MHC class II restricted T cell epitope of an antigenic protein and immediately adjacent thereof, or separated by a linker of at most 7 amino acids, a sequence with a [CST]-xx-C [SEQ ID NO:11] or C-xx-[CST] [SEQ ID NO:12] motif, for increasing the binding affinity of a complex of an MHC II class II molecule and a peptide with a T cell epitope to an MHC class II restricted CD4+ T cell.

A yet further aspect of the invention relates to the use of a [CST]-xx-C [SEQ ID NO:11] or C-xx-[CST] [SEQ ID NO:12] motif for generating a peptide with a T cell epitope and said motif sequence for increasing the binding affinity of an isolated MHC II class II molecule/epitope complex to an MHCII class II restricted CD4+ T cell.

The methods of the present invention can be used, for example in the following applications:

detecting effector CD4+ T cells towards an autoimmune antigen for monitoring an auto immune disease treatment detecting vaccine specific CD4+ T cells for monitoring vaccination efficacy eliminating CD4+ T cells of a recipient prior to a transplantation.

enriching a population of CD4+ T cells prior to expanding said population of cells and optionally expanding the cells in the presence of the peptide or isolating CD4+ T cells at different time points for identifying mutations in the TCR (T cell receptor)

The improved methods and compounds of the present invention find their application in e.g.:

(1) analytical purposes: detection of T cell precursor frequency before vaccination, evaluation of peptide binding affinity for MHC class II complexes, follow-up of specific T cells during the course of vaccination or under immunosuppressive therapy, identification of cells regardless of their biological activity, identification of cells implicated in the mechanism of disease, depletion of specific T cells, and detection of T cells in situ, such in organ biopsies;

(2) Preparative purposes: preparation of specific T cells for evaluation of function, preparation of T cells for culture and purification and TCR sequencing (3) Quality control of cell populations aimed, for instance, at cell therapy;

(4) Therapeutic purposes, including depletion of specific CD4+ T cells before organ grafting.

The structure of MHC class II molecules allows peptides of up to 20 amino acids to be presented to T cells. The core sequence is usually made of 9 amino acids which are inserted into the MHC class II cleft. Flanking regions protrude at both the carboxy- and amino-terminal end of the epitope.

The WO2008017517 patent application describes the use of oxidoreductase motifs inserted into the flanking residues of class II-restricted epitopes for the therapy of a number of diseases. It is demonstrated that the oxidoreductase motif stabilizes the synapse formed between the MHC-peptide complex and cognate TCR, as reported in Carlier et al., *PloS ONE* 7(10): e45366 1-14. The increased synapse formation described therein is supported by experiments with purified APC and CD4+ T cells, which show an increase in number and duration of dimer formation between APC and CD4+ T cells, which results in an effect on various functional properties of CD4+ T cells. An effect on the binding affinity between APC and CD4+ is not discussed in the prior art.

We made the unexpected observation that addition of an oxidoreductase motif within flanking residues of class II epitopes, increases the binding affinity of MHC-epitope complexes with CD4+ T cells, also when the MCH molecules are used as isolated complexes. This allows using peptides with a T cell epitope sequence and a redox motif in the detection and preparation of antigen-specific CD4+ T cells and for all subsequent manipulation of such cells.

The methods and compositions of the present invention allow a specific and high affinity detection of CD4+ T cells.

This specificity and affinity allow more sensitive and specific diagnostic methods.

The specificity and affinity also allows the isolation of CD4+ T cells in higher numbers and higher purity.

The present invention allows detecting CD4+ T cells using isolated MHC class II molecules, outside the context of antigen presentation on intact living cells. The finding that specific and high affinity CD4+ T cell binding can be obtained in the absence of the various interactions that occur between APC and CD4+ T cells is a major finding of the present invention.

The methods of the present invention can be performed on tissues and body fluids, and partially purified fractions thereof.

The methods of the present invention can be performed on samples comprising different types of CD4+ cells and different types of T cells.

The affinity and specificity allows performing cell detection and isolation using a repertoire of techniques which is known for the detection of cell surface antigens using antibodies, or the detection of receptors using ligands. Examples hereof are the immobilisation and manipulation of the MCH-peptide complex on substrates or beads and the labelling of the complex with detectable groups, such as chromophoric groups or magnetic beads.

DETAILED DESCRIPTION

Definitions

The term "peptide" as used herein refers to a molecule comprising an amino acid sequence of connected by peptide bonds, but which can in a particular embodiment comprise non-amino acid structures (like for example a linking organic compound).

A peptide in the context of the present invention comprises at least an MHC class II T cell epitope sequence and a redox motif sequence. These two features are described and defined in further detail below.

In the methods and products of the present application such peptide occurs as a complex with an MHC class II molecule. This complex can be a non-covalent complex of peptide and MHC molecule, or a covalent complex by crosslinking functional groups of peptide and MHC molecule via e.g. SH, COOH, $NH_2$, or OH groups.

In the above complexes the peptide comprising the epitope (8, 9 or 10 amino acids) and the redox motif (4 amino acids) will typically have a length between 12, 13 or 14 amino acids and 16, 17 or 18 amino acids. Depending on the length of the linker and flanking residues the peptide can have a length up to 20, 21, 24, 25 or 30 amino acids.

A specific type of covalent complex is a fusion protein of a peptide with a MHC class II T cell epitope and a redox motif, and an MHC class II molecule (further referred to as "peptide-MHC fusion protein").

Peptides according to the invention can contain any of the conventional 20 amino acids or modified versions thereof, or can contain non-naturally occurring amino-acids incorporated by chemical peptide synthesis or by chemical or enzymatic modification. Of particular interest are modified versions of cysteine with a thiol group such as mercaptovaline, homocysteine or other natural or non-natural amino acids with a thiol function.

"Oxidoreductase motif", "redox motif", "reductase motif" or "motif", refers to a four amino acid sequence with the motif CxxC [SEQ ID NO:13] CxxS [SEQ ID NO:14], CxxT [SEQ ID NO:15], SxxC [SEQ ID NO:16], TxxC [SEQ ID NO:17]. These alternatives can be written as [C]-X(2)-[CS] [SEQ ID NO:18] or [CS]-X(2)-[C] [SEQ ID NO:19].

The term "epitope" refers to one or several portions (which may define a conformational epitope) of an antigenic protein which is/are specifically recognised and bound by an antibody or a portion thereof (Fab', Fab2', etc.) or a receptor presented at the cell surface of a B or T cell lymphocyte, and which is able, by said binding, to induce an immune response.

The term "T cell epitope" in the context of the present invention refers to a dominant, sub-dominant or minor T cell epitope, i.e. a part of an antigenic protein that is specifically recognised and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and able to activate them, among all the possible T cell epitopes of a protein.

The term "MHC class II restricted T cell epitope" in the context of the present invention refers to a T cell epitope which is recognised by MHC class II molecules and consists of a sequence of +/−9 amino acids (8, 9 or 10 AA) which fit in the groove of the MHC II molecule. Within a peptide sequence representing a T cell epitope of 9 AA, the amino acids in the epitope are numbered P1 to P9, amino acids N-terminal of the epitope are numbered P−1, P−2 and so on, amino acids C terminal of the epitope are numbered P+1, P+2 and so on.

The term "antigen" as used herein refers to a structure of a macromolecule, typically protein (with or without polysaccharides) or made of proteic composition comprising one or more hapten (s) and comprising T cell epitopes. The term "antigenic protein" as used herein refers to a protein comprising one or more T cell epitopes. An auto-antigen or auto-antigenic protein as used herein refers to a human or animal protein present in the body, which elicits an immune response within the same human or animal body.

The term "food or pharmaceutical antigenic protein" refers to an antigenic protein naturally present in a food or pharmaceutical product, such as in a vaccine.

The term "natural", when referring to a protein or peptide or a fragment thereof relates to the fact that the sequence is identical to a naturally occurring sequence. This term includes as well wild type sequences as polymorphism and mutants which occur in a population. In contrast therewith the term "artificial" refers to a sequence or peptide which as such does not occur in nature, as peptide or fragment of a protein sequence. Optionally, an artificial sequence is obtained from a natural sequence by limited modifications such as changing one or more amino acids within the naturally occurring sequence or by adding amino acids N- or C-terminally of a naturally occurring sequence.

The term "homologue" as used herein with reference to the epitopes used in the context of the invention, refer to molecules having at least 50%, at least 70%, at least 80%, at least 90%, at least 95% or at least 98% amino acid sequence identity with the naturally occurring epitope, thereby maintaining the ability of the epitope to bind an antibody or cell surface receptor of a B and/or T cell. Particular embodiments of homologues of an epitope correspond to the natural epitope modified in at most three, more particularly in at most 2, most particularly in one amino acid. Specific embodiments hereof are modified epitopes which have a higher binding affinity for CD4+ T cells compared to the unmodified epitope.

The term "derivative" as used herein with reference to the peptides of the invention refers to molecules which contain at least the peptide active portion (i.e. capable of detecting CD4+ T cell) and, in addition thereto comprises a portion which can have different purposes such as stabilising the peptides or altering the pharmacokinetic or pharmacodynamic properties of the peptide.

The term "immune disorders" or "immune diseases" refers to diseases wherein a reaction of the immune system is responsible for or sustains a malfunction or non-physiological situation in an organism. Included in immune disorders are, inter alia, allergic disorders and autoimmune diseases.

The terms "allergic diseases" or "allergic disorders" as used herein refer to diseases characterised by hypersensitivity reactions of the immune system to specific substances called allergens (such as pollen, stings, drugs, or food). Allergy is the ensemble of signs and symptoms observed whenever an atopic individual patient encounters an allergen to which he/she has been sensitised, which may result in the development of various diseases, in particular respiratory diseases and symptoms such as bronchial asthma. Various types of classifications exist and mostly allergic disorders have different names depending upon where in the mammalian body it occurs. "Hypersensitivity" is an undesirable (damaging, discomfort-producing and sometimes fatal) reaction produced in an individual upon exposure to an antigen to which it has become sensitised; "Immediate hypersensitivity" depends of the production of IgE antibodies and is therefore equivalent to allergy.

An "allergen" is defined as a substance, usually a macromolecule or a proteic composition which elicits the production of IgE antibodies in predisposed, particularly genetically disposed, individuals (atopics) patients. Similar definitions are presented in Liebers et al. (1996) Clin. Exp. Allergy 26, 494-516. Examples of allergens are airborne allergens, food allergens, venoms, mite allergens (e.g. Der p 1 and Der p 2).

The terms "autoimmune disease" or "autoimmune disorder" refer to diseases that result from an aberrant immune response of an organism against its own cells and tissues due to a failure of the organism to recognise its own constituent parts (down to the sub-molecular level) as "self". The group of diseases can be divided in two categories, organ-specific and systemic diseases.

Examples of antigens involved in auto-immune diseases, known as autoantigens are thyroglobulin, thyroid peroxidase, TSH receptor, insulin (proinsulin), glutamic acid decarboxylase (GAD), tyrosine phosphatase IA-2, myelin oligodendrocyte protein, heat-shock protein HSP60.

Other antigens include "pathogen-associated antigens", such as viruses, bacteria, mycobacteria or parasites with an intracellular life cycle, or viruses, bacteria and parasites with extracellular life cycle.

The term "allofactor" refers to a protein, peptide or factor (i.e., any molecule) displaying polymorphism when compared between 2 individuals of the same species, and, more in general, any protein, peptide or factor that is inducing an (alloreactive) immune response in the subject receiving the allofactor.

Examples of allofactors are proteins use in a replacement therapy for coagulation defects or fibrinolytic defects, including factor VIII, factor IX and staphylokinase; hormones such as growth hormone or insulin; cytokines and growth factors, such as interferon-alpha, interferon-gamma, GM-CSF and G-CSF; antibodies for the modulation of immune responses, including anti-IgE antibodies in allergic diseases, anti-CD3 and anti-CD4 antibodies in graft rejection and a variety of autoimmune diseases, anti-CD20 antibodies in non-Hodgkin lymphomas, erythropoietin in renal insufficiency.

The term "alloantigen" refers to an antigen generated by protein polymorphism in between 2 individuals of the same species. Examples thereof are MHC class I and/or class II molecules, minor histocompatibility antigens, and tissue-specific alloantigens.

The term "tumor-associated antigen" refers to any protein, peptide or antigen associated with (carried by, produced by, secreted by, etc) a tumor or tumor cell(s). Tumor-associated antigens may be (nearly) exclusively associated with a tumor or tumor cell(s) and not with healthy normal cells or may be overexpressed (e.g., 10 times, 100 times, 1000 times or more) in a tumor or tumor cell(s) compared to healthy normal cells. More particularly a tumor-associated antigen is an antigen capable of being presented (in processed form) by MHC determinants of the tumor cell. Hence, tumor-associated antigens are likely to be associated only with tumours or tumor cells expressing MHC molecules.

Examples are antigens from oncogenes such as MAGE identified in some melanomas; proto-oncogenes, such as cyclin D1 expressed on soft tissues carcinomas such as those of the kidney or parathyroid, as well as in multiple myeloma; virus-derived proteins, such as those from the Epstein-Barr virus in some carcinomas and in some Hodgkin-type lymphomas; surviving factors, which are anti-apoptotic factors such as survivin or bcl2; clonotypic determinants, such as idiotypic determinants derived from B cell receptor in follicular lymphomas or multiple myelomas or T cell receptor determinants in T cell malignancies.

The term "major histocompatibility antigen" refers to molecules belonging to the HLA system in man (H2 in the mouse), which are divided in two general classes. MHC class I molecules are made of a single polymorphic chain containing 3 domains (alpha 1, 2 and 3), which associates with beta 2 microglobulin at cell surface. Class I molecules are encoded by 3 loci, called A, B and C in humans. Such molecules present peptides to T lymphocytes of the CD8+ subset.

"Class II molecules" as occurring on cells are transmembrane proteins consisting of 2 polymorphic chains, each containing 2 chains (alpha 1 and 2, and beta 1 and 2). These class II molecules are encoded by 3 loci, DP, DQ and DR in man.

For the purpose of the present invention it is required and sufficient that the MCH molecule-T cell epitope complex can bind to a CD4+ T cell.

MHC molecules can be isolated from cells or produced in recombinant expression systems.

"Isolated" when referring to MHC class II proteins and complexes with peptides refers to compounds, obtained via recombinant processes or (partial) purification of cells, including lysates and fractions of lysates.

The term "minor histocompatibility antigen" refers to peptides that are derived from normal cellular proteins and are presented by MHC belonging to the class I and/or the class II complexes. Any genetic polymorphism that qualitatively or quantitatively affects the display of such peptides at the cell surface can give rise to a minor histocompatibility antigen.

"CD4+ T cells" are characterized by the surface expression of CD4 glycoprotein. CD4+ cells which are applicable in the context of the present invention include:

Tregs (regulatory T cells) which are involved in active suppression of inappropriate immune responses. These cells are CD4+, CD25+, FoxP3+ cells.

Induced Tregs such as Tr1 or Th3 CD4+ T cells, involved in suppression of inappropriate immune responses, said cells characterized by any combination of surface markers such as Lag3$^{hi}$ and CD49b, intracellular IL-10 and TGF-beta, and granzyme B.

Naïve CD4+ T cells which express CD45A and CD197, have a low or intermediate expression of CD44, and a low cytokine production with no preferred pathway.

Polarised CD4+ cells which have a high CD44 expression and the production of a restricted set of cytokines.

Cytolytic CD4+ T cells (cCD4+ T cells) which have been characterised in detail in WO2009/101207 and are characterized by i.a. the absence of FoxP3 expression.

The term "viral vector protein" when used herein refers to any protein or peptide derived from a viral vector itself, and which is encoded by the backbone of the vector. It does not refer to the therapeutic protein itself which is cloned in the viral vector. In the exceptional event that a viral protein would be cloned in a viral vector, this protein still classifies as a therapeutic protein and not as a viral vector protein. Typically such viral vector proteins are antigenic and comprise one or more epitopes such as T-cell epitopes.

Examples of proteins encountered in the backbone of a vector are those obtained from RNA viruses such as gamma-retroviruses and lentiviruses and from DNA viruses such as adenoviruses, adeno-associated viruses, herpes viruses and poxviruses.

The term "alloreactivity" refers to an immune response that is directed towards allelic differences between the graft recipient and the donor. Alloreactivity applies to antibodies and to T cells. The present invention relies entirely on T cell alloreactivity, which is based on T cell recognition of alloantigens presented in the context of MHC determinants as peptide-MHC complexes.

"Complex" in the context of the present invention relates to an association of one or more MHC class II molecules with a peptide comprising an epitope. The association can be a non-covalent association by the spontaneous binding of the peptide with the MHC molecule via salt bridges, hydrogen bridges and hydrophobic contacts. The association can also be a covalent association via chemical crosslinking using crosslinking agents and bifunctional molecules.

In a specific type of complex the MCH class II molecule and the peptide is a recombinant fusion protein (a so called peptide-MHC fusion proteins).

"Motifs" of amino acid sequences are written herein according to the format of Prosite. The symbol X is used for a position where any amino acid is accepted.

Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen -. Repetition of an identical element within a motif can be indicated by placing behind that element a numerical value or a numerical range between parentheses. For example: X(2) corresponds to X-X, X(2, 4) corresponds to X-X or X-X-X or X-X-X-X, A(3) corresponds to A-A-A.

The present invention is based upon the finding that a peptide, comprising a T cell epitope and a peptide sequence having reducing activity is capable of detecting CD4+ T cells.

Accordingly, in its broadest sense, the invention relates to methods and compositions of peptides which comprise at least one T-cell epitope of an antigen (self or non-self) with a potential to interact with a CD4+ T cell TCR, coupled to a peptide with a thioreductase sequence motif. The T cell epitope and the redox motif sequence are optionally separated by a linker sequence. In further optional embodiments the peptide additionally comprises additional "flanking" sequences.

Typical embodiments of peptides used in the methods and compositions of the invention can be schematically represented as Flanking sequence-Epitope-Linker-Motif-Flanking sequence or Flanking sequence-Motif-Linker-Epitope-Flanking, wherein "Epitope" represents a T-cell epitope of an antigen (self or non-self) with a potential to react with the TCR of CD4+ T lymphocytes, "Linker" represents an optional linker of between 0 and 7 amino acids, "Motif" represents a four amino acids oxidoreductase motif, and "Flanking sequence" optional additional amino acids. The reducing activity can be assayed for its ability to reduce a sulfhydryl group such as in the insulin solubility assay wherein the solubility of insulin is altered upon reduction, or with a fluorescence-labelled insulin. Alternatively, the reducing activity can be evaluated in a fluorometric assay in which a peptide is incubated with a oxidized substrate freeing fluorescence after being reduced. The peptide with the oxidoreductase may be coupled at the amino-terminus side of the T-cell epitope or at the carboxy-terminus of the T-cell epitope. Peptide fragments with reducing activity are encountered in thioreductases which are small disulfide reducing enzymes including glutaredoxins, nucleoredoxins, thioredoxins and other thiol/disulfide oxydoreductases (Holmgren (2000) *Antioxid Redox Signal* 2, 811-820; Jacquot et al. (2002) *Biochem Pharm* 64, 1065-1069). They are multifunctional, ubiquitous and found in many prokaryotes and eukaryotes. They exert reducing activity for disulfide bonds on proteins (such as enzymes) through redox active cysteines within conserved active domain consensus sequences: C-X(2)-C [SEQ ID NO:13], C-X(2)-S [SEQ ID NO:14], C-X(2)-T [SEQ ID NO:15], S-X(2)-C [SEQ ID NO:16], T-X(2)-C [SEQ ID NO:17] (Fomenko et al. (2003) *Biochemistry* 42, 11214-11225; Fomenko et al. (2002) *Prot. Science* 11: 2285-2296), in which X stands for any amino acid. Such domains are also found in larger proteins such as protein disulfide isomerase (PDI) and phosphoinositide-specific phospholipase C.

In order to have reducing activity, the cysteines present in the motif should not occur as part of a cystine disulfide bridge. Also methylated versions of cysteine are contemplated in the peptides used in the present invention.

As explained in detail further on, peptides can be made by chemical synthesis, which allows the incorporation of non-natural amino acids. Accordingly, in the motif of reducing compounds, C represents either cysteine or another amino acids with a thiol group such as mercaptovaline, homocysteine or other natural or non-natural amino acids with a thiol function. In order to have reducing activity, the cysteines present in the motif should not occur as part of a cystine disulfide bridge.

The amino acid X in the [CST]-X(2)-[CST] [SEQ ID NO:20] motif can be any natural amino acid, including S, C, or T or can be a non-natural amino acid. In particular embodiments X is an amino acid with a small side chain such as Gly, Ala, Ser or Thr. In further particular embodiments at least one X in the [CST]-X(2)-[CST] [SEQ ID NO:20] motif is His, Pro or Tyr. Other embodiments refer to peptides with the motif wherein one or both X are not cysteine. Other embodiments refer to peptides wherein cysteines do not occur as, two, three or four consecutive cysteine, such as for example in tetracysteine tags.

Further embodiments refer to peptides wherein the one or two cysteines of the[C]-X(2)-[CST] [SEQ ID NO:12] or [CST]-X(2)-[C] [SEQ ID NO:11] motif are the only cysteines in the non-epitope part of the peptide. More specifically the linker between the epitope and the motif does not contain a cysteine.

In certain embodiments wherein the epitope sequence itself comprises no cysteine residues, the one or two cysteines of the redox motif is/are the only cysteines in the peptide.

In the peptides comprising the motif described above as the reducing compound, the motif is located such that, when the epitope fits into the MHC groove, the motif remains outside of the MHC binding groove. The motif is placed either immediately adjacent to the epitope sequence within the peptide (i.e. there are no amino acids in-between the epitope sequence and the oxidoreductase motif ("linker of 0 amino acid")) or is separated from the T cell epitope by a linker. More particularly, the linker comprises an amino acid sequence of 7 amino acids or less. Most particularly, the linker comprises 1, 2, 3, or 4 amino acids. Alternatively, a linker may comprise 5, 6, or 7 amino acids. When the motif sequence is adjacent to the epitope sequence this is indicated as position P−4 to P−1 or P+1 to P+4 compared to the epitope sequence. The peptides can further comprise additional short amino acid sequences N or C-terminally of the (artificial) sequence comprising the T cell epitope and the reducing compound (motif). Such an amino acid sequence is generally referred to herein as a 'flanking sequence'. In further embodiments, a short amino acid sequence may be present N and/or C terminally of the reducing compound and/or epitope sequence in the peptide. More particularly a flanking sequence is a sequence of between 1 and 7 amino acids, most particularly a sequence of 2 amino acids.

As can be understood the length of a peptide in a non-covalent complex with an MHC molecule is at least 12-14 amino acids (8-10 AA epitope+4 AA redox motif). But the length increases with the presence of linker sequence (additional 7 AA) and a flanking sequence at one (additional 7 AA) or both (additional 14 AA) ends. Typically sequences are used with a length between 12 up to 20 or 25 amino acids.

In particular embodiments, the motif is located N-terminal from the epitope.

In other embodiments, a motif is located both N-terminal and C-terminal from the epitope.

In further particular embodiments, where the motif present in the peptide contains one cysteine, this cysteine is present in the motif in the position remote from the epitope, thus the motif occurs as C-X(2)-T [SEQ ID NO:15] or C-X(2)-S [SEQ ID NO:14] N-terminally of the epitope or occurs as T-X(2)-C [SEQ ID NO:17] or S-X(2)-C [SEQ ID NO:16] C-terminally of the epitope.

In certain embodiments of the present invention, peptides are provided comprising one epitope sequence and a motif sequence. In further particular embodiments, the motif occurs several times (1, 2 or even 3 times) in the peptide, for example as repeats of the motif which can be spaced from each other by one or more amino acids (e.g. CXXC X CXXC X CXXC [SEQ ID NO:21]), or as repeats which overlap with each other such as in the sequence CXXCXXCXXC [SEQ ID NO:22]. Alternatively, one or more motifs are provided at both the N and the C terminus of the T cell epitope sequence.

Accordingly, peptides comprise, in addition to a reducing compound, a T cell epitope derived from an antigen, typically an allergen or an auto-antigen, a pathogen-associated antigen, a viral vector antigen, a tumor-associated antigen, an allofactor or a alloantigen, depending on the application. As described below a T cell epitope in a protein sequence can be identified by functional assays and/or one or more in silico prediction assays. The amino acids in a T cell epitope sequence are numbered according to their position in the binding groove of the MHC proteins. In particular embodiments, the T-cell epitope present within the peptides of the invention consists of between 8 and 20 amino acids, yet more particularly of between 8 and 16 amino acids, yet most particularly consists of 8, 9, 10, 11, 12, 13, 14, 15 or 16 amino acids. In a more particular embodiment, the T cell epitope consists of a sequence of 8, 9, or 10 amino acids. The T cell epitope sequence is an epitope sequence which fits into the cleft of an MHC II protein, also known as an MHC class II restricted T cell epitope.

The T cell epitope of the peptides of the present invention can correspond either to a natural epitope sequence of a protein or can be a modified version thereof, provided the modified T cell epitope retains its ability to bind within the MHC cleft, similar to the natural T cell epitope sequence.

The modified T cell epitope can have the same binding affinity for the MHC protein as the natural epitope, but can also have a lower or higher affinity. In particular embodiments the binding affinity of the modified peptide is no less than 10-fold less than the original peptide, more particularly no less than 5 times less. It is a finding of the present invention that the peptides of the present invention have a stabilising effect on protein complexes formed between the pMHC and the complementary TCR. Accordingly, the stabilising effect of the peptide-MHC complex compensates for the lowered affinity of the modified epitope for the MHC molecule. An example hereof is the Ile28Asn substitution of Der p 2 peptide p21-35, which despite a lower affinity for the MHC II cleft, is capable of eliciting the same T cell response as the natural Der p 2 peptide p21-35.

As detailed above, in particular embodiments, the peptides of the present invention comprise a reducing motif as described herein linked to a T cell epitope sequence. According to a particular embodiment the peptides are peptides from proteins which do not comprise within their native natural sequence an amino acid sequence with redox properties in the vicinity (i.e. within a sequence of 11 amino acids N or C terminally) of the epitope of interest, more specifically which do not comprise in their native natural sequence a consensus sequence of thioredoxin, glutaredoxin or thioreductases or homologues thereof, in the vicinity of the epitope of interest.

The presence of a reductase motif in the vicinity of an epitope in an antigen protein is very rare. In some embodiments the peptide with the epitope and the motif is a fragment of a naturally occur protein. In most embodiments the peptide is an artificial peptide, wherein the sequence around the epitope has been modified to introduce at least the redox motif.

The identification of a suitable T cell epitope of an antigenic protein for use in the generation of peptides as described in the methods above is detailed below.

The identification and selection of a T-cell epitope from such antigenic proteins for use in the context of the present invention is known to a person skilled in the art.

Non-natural (or modified) T-cell epitopes can further optionally be tested on their binding affinity to MHC class II molecules. This can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al. (2000) *J. Immunol.* 164, 3177-3184.

Additionally and/or alternatively, one or more in vitro algorithms can be used to identify a T cell epitope sequence within an antigenic protein. Suitable algorithms include, but are not limited to those found on the following websites:
antigen.i2r.a-star.edu.sg/predBalbc/;
imtech.res.in/raghava/mhcbn/;
syfpeithi.de/home.htm;
bs.informatik.uni-tuebingen.de/SVMHC;
bio.dfci.harvard.edu/Tools/antigenic.html;
jenner.ac.uk/MHCPred/.

More particularly, such algorithms allow the prediction within an antigenic protein of one or more nonapeptide sequences which will fit into the groove of an MHC II molecule.

Peptides and proteins can be generated using recombinant DNA techniques, in bacteria, yeast, insect cells, plant cells or mammalian cells. Peptides of limited length, can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine.

Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry. During peptide synthesis several protecting groups are used. For example hydroxyl and carboxyl functionalities are protected by t-butyl group, Lysine and tryptophan are protected by t-Boc group, and asparagine, glutamine, cysteine and histidine are protected by trityl group, and arginine is protected by the pbf group. In particular embodiments, such protecting groups can be left on the peptide after synthesis.

Alternatively, the peptides, and especially fusion proteins of peptide and MHC molecule can be synthesized by using nucleic acid molecules which encode the peptides of this invention in an appropriate expression vector which include the encoding nucleotide sequences. Such DNA molecules may be readily prepared using an automated DNA synthesizer and the well-known codon-amino acid relationship of the genetic code. Such a DNA molecule also may be obtained as genomic DNA or as cDNA using oligonucleotide probes and conventional hybridization methodologies. Such DNA molecules may be incorporated into expression vectors, including plasmids, which are adapted for the expression of the DNA and production of the polypeptide in a suitable host such as bacterium, e.g. *Escherichia coli*, yeast cell, animal cell or plant cell.

The physical and chemical properties of a peptide of interest (e.g. solubility, stability) are examined to determine whether the peptide is/would be suitable for use for applications as defined for the present invention. Typically this is optimised by adjusting the sequence of the peptide. Optionally, the peptide can be modified after synthesis (chemical modifications e.g. adding/deleting functional groups) using techniques known in the art.

Peptides are loaded on class II MHC molecules. In one embodiment, cells presenting the relevant MHC class II molecule are incubated with the peptide. The cells are then used as such to bind the cognate TCR, either in soluble phase followed by facs analysis, or after insolubilisation on plates or on beads. These techniques are well described in the art. In an alternative embodiment, cells are lysed and the MHC class II molecules loaded with peptide are prepared by, for instance, chromatography. The pMHC complexes, with or without labelling, can then be used in soluble phase to interact with a population of CD4+ T cells, or insolubilized on plates or beads or any suitable solid-phase support for the detection of CD4+ T cells.

In another embodiment, MHC class II molecules are produced by cDNA technology using cell transfection or transduction. The cDNA construct can contain the full-length class II molecule with its intramembranous sequences for surface anchoring and use of cells as described above, or without the intramembranous sequence for secretion. Such secreted class II molecules can be purified and used as described above, in soluble forms or after insolubilisation on a solid surface such as plates or beads.

WO2011147894 discloses chimeric proteins of an alpha-chain and beta-chain of a MHC-class II protein, a linker and an epitope of interest, wherein the epitope is linked to the a-chain via the linker.

Basic leucine zippers, cysteine bridges (see e.g. WO2011101681), or chemical crosslinking can be used to connect the alpha and beta chain of the MHC molecules. Recombinant versions, lacking the transmembrane domains are also described in WO2011101681. Fusion proteins combining two MHC molecules are described, optionally as fusion protein with the epitope sequence (WO2011147894). WO1998006749 describes fusion proteins of an extracellular binding domain of an MHC II molecule and dimerization domain.

The MHC molecules can be further modified by binding moieties (peptide tags such as His tag, a binding moiety such as biotin, binding proteins such as GST, MBP, antibody tags such as HA tags.)

The MHC molecules can also be modified with detectable labels such as chromophoric groups, radioactive labels, magnetic beads.

In yet another embodiment, the cDNA construct encompassing class II MHC molecules also comprises the sequence of the peptide, so that the engineered molecule constitutively expresses the peptide in fusion with the MHC molecule. It is advantageous in this embodiment to include a linker in between the sequence of class II molecule and the sequence of the peptide, so as to allow proper folding and presentation of the peptide into the cleft of the class II molecule. These linkers are typically a polypeptide sequence of about 15 amino acids with serines and/or glycines to provide enough flexibility for the epitope to tether on the beta chains. The linker can further comprise a protease specific recognition site (e.g. for thrombin) such that after expression and folding, the peptide is presented in its normal configuration.

Soluble forms of MHC class II molecules before or after loading with a peptide, or molecules constitutively expressing the peptide can be used in the form of dimers or polymers, either by reacting several molecules between each other or by insolubilizing such molecules onto a solid phase such as beads or plates. These methods are described in the art.

MHC molecules can occur as multimers, such as tetramers (reviewed in Nepom, cited above) or dextramers (Massilamany (2011) *BMC Immunol.* 12, 40).

T cell epitopes of the present invention are thought to exert their properties by creating a disulfide bridge between the thioreductase motif and the CD4 molecule. This mechanism of action is substantiated by experimental data (see examples below), but there is no intention to restrict the present invention to this specific mechanism of action.

The methods and tools of the present invention can be used in various applications such as detection, preparation or depletion of antigen-specific CD4+ T cells for diagnosis purposes, phenotypic or functional evaluation, or T cell receptor (TCR) cloning. The CD4+ cell that are obtained our technology could also serve for high sequencing RNA, proteomics and to prepare material for crystallization of T cell receptors.

EXAMPLES

Example 1. Use of Tetramers of MHC Class II Molecules for the Detection of MOG-Specific CD4+ T Lymphocytes in the Naïve Human T Cell Repertoire Multiple sclerosis is a chronic demyelination disease in which CD4+ T cells towards auto antigens such as the myelin oligodendrocytic glycoprotein (MOG) play a key role. The migration of effector cells through the brain-blood barrier elicits brain tissue destruction.

Such effector CD4+ T cells are generated from peripheral blood naïve T cells after cognate interaction with antigen-presenting cells presenting the MOG epitope within MHC class II complexes. Enumerating (i.e. identifying and quantifying) MOG-specific naïve CD4+ T cells is therefore predictive of disease outcome. However, the frequency of naïve T cell and affinity for MOG epitope are low, which prevents their detection by conventional technology, as for instance soluble tetramers of MHC class II molecules loaded with the MOG epitope.

One of such major MHC class II epitope of MOG is presented by molecules of the class II DR2 haplotype with the common DRB1*1501 allele being expressed by ±75% of patients affected by multiple sclerosis.

Naïve CD4+ T cells are prepared from the peripheral repertoire of DRB1*1501+ subjects susceptible to suffer from multiple sclerosis, using magnetic beads to remove CD4(−) cells and memory cells, as described in the art. Tetramers of DRB1*1501 are made as known in the art (Kasprowicz V et al. (2006) *J. Virol.* 80, 11209-112017), including a fluorescent label such as Ficoerythrin. A synthetic peptide is produced, which encompasses the corresponding class II-restricted MOG T cell epitope and a thioreductase motif CGPCSRVVHLYRNGK D [SEQ ID NO: 1], which corresponds to amino acid residues 47-58 of the MOG protein.

Tetramers are loaded with peptide of SEQ ID 1 overnight at room temperature in the appropriate buffer conditions as known in the art. Loaded tetramers are then washed and incubated with naïve CD4+ T cells for 2 h at 37° C. The suspension is then read with a fluorescence-activated cell sorting (facs) system and the proportion of naïve cells specific to the MOG peptide evaluated Control experiments are performed with MHC complex with the same peptide without thioreductase motif. SRVVHLYRNGKD [SEQ ID NO:2].

The experiment shows that only the MHC complex with the peptide containing a thioreductase motif (SEQ ID 1) is able to detect naïve CD4+ T cells specific to the MOG 37-52 sequence.

Example 2. Use of Tetramers of MHC Class II Molecules for the Follow-Up of Specific CD4+ T Cells During Vaccination and for Modulation of the Vaccination Strategy The effectiveness of vaccination for infectious diseases depends on the number of CD4+ T cells which can be activated by such vaccination. An early and predictive sign of successful vaccination can be found in the increase in the number of vaccine-specific CD4+ T cells, a useful parameter to decide whether the vaccination strategy has to be modified by, for instance, increasing the number of vaccine administrations. Influenza virus vaccination is a significant example in so far as there is only a loose correlation between the concentration of specific antibodies and the robustness of protection.

A major MHC class II-restricted epitope of the virus is located in the hemagglutinin protein. Peptide of sequence CGHCKYVKQNTLKHEMAGG (SEQ ID NO: 3 is therefore produced and loaded onto MHC class II tetramers as described in example 1. A control experiment is performed with tetramers loaded with a peptide with the same epitope but which does not include a thioreductase motif KYVKQNTLK HEMAGG (SEQ ID NO: 4) CD4+ T cells are prepared from peripheral blood in subjects prior to and 3 weeks after influenza vaccine administration. Such cells are incubated with fluorescence-labeled MHC class II tetramers loaded with peptide of SEQ ID 3. The number of cells per million identified by fluorescence labeling is then counted using a facs device.

It is shown that a higher number of CD4+ T cells are detected in peripheral blood when MHC class II tetramers are loaded with peptide of SEQ ID 3 than with peptide of SEQ ID 4. Further, the number of specific CD4+ T cells obtained 3 weeks after the start of the vaccination is determined and the concentration of hemagglutinin-specific antibodies is measured 8 weeks after the start of such vaccination. A close relationship is observed between the number of CD4+ T cells detected using tetramers loaded with peptides of SEQ ID 3 and the concentration of the hemagglutinin-specific antibodies.

Such a correlation between CD4+ cells and hemagglutinin-specific antibodies is not observed when tetramers with the peptide with SEQ ID NO: 3 (i.e. without reducing motif) are to quantify CD4+ cells.

This correlation between CD4+ cells at three weeks and hemagglutinin-specific antibodies at 8 weeks, allows predicting at an early stage after vaccination whether sufficient hemagglutinin-specific antibodies will be formed later on.

Accordingly, subjects with too low a number of CD4+ T cells at 3 weeks are further injected with the vaccine. This method makes it possible to restrict a second vaccination to those individuals which are effectively in need of a re-vaccination.

Example 3. Depletion of Donor-Specific Specific CD4+ T Cells from the Host Repertoire to Improve Bone Marrow Grafting Bone marrow rejection occurs when CD4+ T lymphocytes from the recipient react towards alloantigens from the donor bone marrow. Both CD4 and CD8 cells are involved in this process, but CD4 cells are required to activate CD8+ T cells. Eliminating recipient's CD4+ T cells would therefore allow successful grafting. Removal of CD4+ T cells specific for alloantigens require a high performance affinity adsorption because of the low frequency of such cells.

The prior art MHC-T cell epitope complexes have not the required affinity to detect and to isolate the relevant CD4+ cells.

In the mouse model, male bone marrow is rejected by syngeneic females due to recognition of H-Y encoded antigens among which the Dby protein plays a major role. A majority of CD4+ T cells recognize an epitope made of residues FNSNRANSS of the murine Dby antigen which is encoded by the H-Y chromosome A synthetic peptide made of this class II restricted T cell epitope with a thioreductase motif is produced, corresponding to CHGCFNSNRANSS [SEQ ID NO:5] and the corresponding Dby peptide in natural configuration is produced as a control, namely CHGCFNSNRANSS [SEQ ID NO:6].

Lymphocytes from the spleen of female H-2b mice are prepared by magnetic bead sorting. The cells are then incubated with a suspension of beads coated with class II H-2b molecules and loaded with peptide of SEQ ID 5 or of SEQ ID 6. Lymphocytes T cells, containing all CD4+ T cells not retained on beads and CD8+ T cells, are used to reconstitute RAG2 KO mice, which are then engrafted by the bone marrow of a male syngeneic donor. RAG2 KO mice have no functional adaptive immune system and are therefore unable to reject the graft. Rejection is thereby depending only of cells present in the passively transferred population.

It is shown that mice with the depleted Dby specific CD4+ T cells accept the bone marrow, whilst RAG2 KO mice reconstituted with non-depleted Dby-specific CD4+ cells strongly reject it. Depletion of CD4+ T cells with beads coated with control peptide of SEQ ID 6 shows no improvement of graft acceptance.

It is therefore concluded that depletion of CD4+ T cells by beads coated with peptides containing a thioreductase motif is much more efficient in controlling the host response to the allogenic bone marrow.

Example 4. Preparation of Specific CD4+ T Cells for Cell Therapy

Cell therapy consists in isolating cells from a donor, purifying and expanding the relevant cell population in vitro and re-administering his/her own cells to the donor. The success of such approach is highly dependent on the efficacy of the method used to isolate cells.

In insulin-dependent diabetes mellitus (IDDM) the GAD65 antigen plays an important pathogenetic role. Modifying the properties of GAD65-specific CD4+ T cells, as described in WO2008017517, allows to suppress the deleterious response against Langerhans beta cells.

NOD (non-obese diabetic) mice spontaneously develop diabetes by progressive destruction of insulin-producing Langerhans islet cells. NOD mice are considered as a representative pre-clinical model of human IDDM. Effector CD4+ T cells against GAD65 are prepared from the spleen of diseased animals by first depleting non-CD4+ cells. CD4+ cells are then incubated with class II tetramers loaded with a GAD65 class II restricted epitope encompassing a thioreductase motif in flanking residues.

The sequence of the peptide is therefore CRLCKVAP-VIKARMM (GAD65 524-543) (SEQ ID NO: 7) A peptide of GAD65 without thioreductase motif is prepared for control experiments KVAPVIKARMM (SEQ ID NO: 8).

Cells are then sorted by facs according to their binding of peptide-loaded tetramers. Positive cells are then maintained in culture and stimulated with APC loaded with peptide of SEQ ID 7 to generate cytolytic CD4+ T cells, as described in the WO2008017517 patent application. It is observed that the yield of GAD65-specific cytolytic CD4+ T cells is significantly increased when peptide of SEQ ID 7 is used instead of peptide of SEQ ID 8.

The yield of GAD65-specific cytolytic CD4+ T cells is also higher than in the method disclosed in WO2008017517, wherein a peptide with SEQ ID NO 7 was added to T cells obtained from the spleen of NOD mice.

Cells expanded in vitro and having acquired cytolytic properties are used for cell transfer in NOD mice and are shown to prevent or suppress the development of IDDM.

Example 5. Preparation of CD4+ T Cells for T Cell Receptor (TCR) Sequencing

One of the risk factors for disease development is linked to the repertoire of T cells available in peripheral blood. Currently, however, an association between TCR family usage and higher risk of developing disease, is identified only when disease is patent, namely when sufficient expansion of specific T cells has already occurred, thereby allowing detection using currently available methods. Detecting such cells before the development of disease would be of much interest and could, in addition, provide the possibility of purging such cells from the repertoire, as described in example 3 above. An example is provided by T cells in germline configuration which recognize an epitope located in the 9-23 region of insulin (Nakayama et al. (2012), *Diabetes* 61, 857-865, 2012).

Further, during the course of an immune response involving CD4+ T cells, be it in the framework of a spontaneous disease or as a result of vaccination, there is an increase in TCR affinity resulting from selection of T cell clones with higher natural affinity and from mutations introduced in the hypervariable parts of the TCR. It would be advantageous to follow such TCR usage and/or mutations in a number of situations. Thus, maturation of the T cell repertoire during a vaccination with weak antigens is predictive of protection. Further, in autoimmune diseases, change in TCR affinity due to mutations could be predictive of disease worsening.

TCR family usage and detection of TCR mutations requires receptor sequencing, which can only be carried out on highly purified cells obtained in sufficient numbers. The invention allows such methods, as illustrated by the following example.

Expression of human DQ8 MHC class II molecule is associated with reactivity to a major epitope of insulin, located in the beta chain of insulin within the amino acid sequence 9-23. Human peripheral blood naïve T cell repertoire frequently contains cells expressing germline encoded alpha chain sequences, called Trav13-1, associated with various beta chain sequences, but which are sufficient as to confer a low affinity reaction with the B9-23 insulin epitope when presented by DQ8.

Peptides encompassing the sequences of the B9-23 epitope with a thioreductase motif and a one amino acid glycine linker are produced, namely CGHCGSHLVEALYLVCGERG INS9-23 (SEQ ID 9) and control peptides without thioreductase motif and linker SHLVEALYLVCGERG INS9-23 (SEQ ID 10)

Tetramers of DQ8 are produced and loaded with each one of peptides of SEQ ID 9 or SEQ ID 10. Loaded tetramers are incubated with human peripheral blood CD4+ T cells. Cells are washed, analysed by facs and sorted out. Cells are then washed from tetramers and used for TCR alpha chain sequencing using corresponding primers. It is shown that only cells prepared by tetramers loaded with peptide of SEQ ID 9 (containing a thioreductase motif) are obtained in sufficient number as to allow TCR sequencing.

It is therefore concluded that T cell epitopes containing a thioreductase motif are useful to detect and prepare cells carrying a given TCR in numbers sufficient as to allow TCR sequencing.

Sequences Disclosed in the Application:

(MOG 47-58)
[SEQ ID NO: 1]
CGPCSRVVHLYRNGKD (MOG 47-58)
[SEQ ID NO: 2]
SRVVHLYRNGKD (influenza hemagglutinin)
[SEQ ID NO: 3]
CGHCKYVKQNTLKHEMAGG (influenza hemagglutinin)
[SEQ ID NO: 4]
KYVKQNTLKHEMAGG (Dby)
[SEQ ID NO: 5]
CHGCFNSNRANSS (Dby)
[SEQ ID NO: 6]
FNSNRANSS (GAD65 524-543)
[SEQ ID NO: 7]
CRLCKVAPVIKARMM (GAD65 524-543)
[SEQ ID NO: 8]
KVAPVIKARMM (INS9-23)
[SEQ ID NO: 9]
CGHCGSHLVEALYLVCGERG (INS9-23)
[SEQ ID NO: 10]
SHLVEALYLVCGERG

The invention claimed is:

1. An isolated complex of:
    a Major Histocompatibility Complex (MHC) class II molecule and
    a peptide consisting essentially of (i) an MHC class II restricted CD4+ T cell epitope of an antigenic protein and (ii) a redox motif of [CST]-X-X-C (SEQ ID NO: 11) or C-X-X-[CST] (SEQ ID NO: 12), which are immediately adjacent to each other or separated by a linker of at most 7 amino acids, wherein X is any amino acid, C is cysteine and [CST] is an amino acid selected from cysteine, serine and threonine.

2. The complex according to claim 1, wherein said redox motif is C-X-X-C (SEQ ID NO: 13).

3. The complex according to claim 1, wherein said MHC class II restricted CD4+ T-cell epitope and redox motif are separated by a linker of at most 4 amino acids.

4. The complex according to claim 1, wherein said complex between said peptide and said MHC class II molecule is a covalently bound complex.

5. The complex according to claim 4, wherein said covalently bound complex is a fusion protein of said MHC class II molecule with said peptide.

6. The complex according to claim 1, wherein said complex is attached to a bead or a plate.

7. An in vitro method for detecting class II restricted CD4+ T cells in a sample comprising the steps of:
    providing a sample comprising cells;
    contacting the sample with a complex according to claim 1; and
    measuring the binding of said complex with cells in said sample, wherein the binding of said complex to said cells is indicative of CD4+ T cells being present in said sample.

8. The method according to claim 7, wherein said redox motif is C-X-X-C (SEQ ID NO: 13).

9. The method according to claim 7, wherein said MHC class II restricted CD4+ T-cell epitope and redox motif are separated by a linker of at most 4 amino acids.

10. The method according to claim 7, wherein said peptide occurs in a non-covalent complex with the MHC class II molecule and has a length of between 12 and 20 amino acids.

11. The method according to claim 7, wherein said complex is a fusion protein of said MCH class II molecule with said peptide.

12. The method according to claim 7, wherein the sample is a blood sample or a tissue sample.

13. The method according to claim 12, wherein the tissue sample is synovial fluid from a rheumatoid arthritis patient or pleural fluid of a patient with infectious pneumonia.

14. The method according to claim 12, wherein said complex is attached to an insoluble carrier or a substrate.

15. The method according to claim 12, further comprising the step of detecting or isolating subpopulations of detected CD4+ T cells.

16. The method according to claim 7, wherein said CD4+ T cells are one or more selected from the group consisting of Tregs, induced Tregs such as Tr1 or Th3, naïve CD4+ T cells, polarised CD4+ T cells, and cytolytic CD4+ T cells.

17. The method according to claim 7, wherein said sample comprises one or more cells selected from the group consisting of naïve CD4+ T cells, antigen-exposed CD4+ T cells, CD4+ T cells obtained during therapy or during vaccination, and CD4+ T cells in a tissue.

18. The method according to claim 7, wherein said epitope sequence of said peptide is identical to the epitope sequence of said antigenic protein or wherein, the MHC class II anchoring residues of the epitope sequence of said peptide are modified compared to the epitope sequence of said antigenic protein in order to modulate the binding affinity of an epitope to CD4+ cells.

19. The method according to claim 7, wherein said MHC class II molecule in the complex is a multimer.

20. The method according to claim 7, wherein said complex is a soluble complex.

21. The method according to claim 7, further comprising the step of isolating CD4+ T cells which are bound to said complex.

* * * * *